(12) United States Patent
Spee et al.

(10) Patent No.: US 9,127,052 B2
(45) Date of Patent: Sep. 8, 2015

(54) LLT-1 ANTIBODIES WITH NEW FUNCTIONAL PROPERTIES

(75) Inventors: Petrus Johannes Louis Spee, Allerod (DK); Peter Andreas Nicolai Reumert Wagtmann, Rungsted Kyst (DK); Stefan Zahn, Bellerup (DK); Elisabeth D. Galsgaard, Naerum (DK); Birgitte Friedrichsen, Gentofte (DK); Véronique Braud, Grasse (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 13/807,505

(22) PCT Filed: Jun. 28, 2011

(86) PCT No.: PCT/EP2011/060819
§ 371 (c)(1),
(2), (4) Date: Mar. 14, 2013

(87) PCT Pub. No.: WO2012/000994
PCT Pub. Date: Jan. 5, 2012

(65) Prior Publication Data
US 2013/0164299 A1 Jun. 27, 2013

Related U.S. Application Data

(60) Provisional application No. 61/360,520, filed on Jul. 1, 2010, provisional application No. 61/362,319, filed on Jul. 8, 2010, provisional application No. 61/364,156, filed on Jul. 14, 2010.

(30) Foreign Application Priority Data

Jun. 29, 2010 (EP) ..................... 10167668
Jul. 1, 2010 (EP) ..................... 10168095
Jul. 13, 2010 (EP) ..................... 10169409

(51) Int. Cl.
*C07K 16/28* (2006.01)
*C07K 16/18* (2006.01)

(52) U.S. Cl.
CPC ............ *C07K 16/18* (2013.01); *C07K 16/2851* (2013.01); *C07K 2317/24* (2013.01); *C07K 2317/73* (2013.01); *C07K 2317/76* (2013.01); *C07K 2317/92* (2013.01)

(58) Field of Classification Search
CPC .................. C07K 16/18; C07K 16/28
See application file for complete search history.

(56) References Cited

U.S. PATENT DOCUMENTS 6,455,683 B1 * 9/2002 Yang et al. .................... 536/23.1
2006/0002892 A1 1/2006 Mathew et al.

FOREIGN PATENT DOCUMENTS

| WO | 95/23813 A1 | 9/1995 |
|----|-------------|--------|
| WO | 0105964 A1 | 1/2001 |
| WO | 2004069183 A2 | 8/2004 |
| WO | 2005060368 A2 | 7/2005 |
| WO | 2006010603 A1 | 2/2006 |
| WO | 2009094148 A2 | 7/2009 |
| WO | 2010050528 A1 | 5/2010 |
| WO | 2010051105 A1 | 5/2010 |

OTHER PUBLICATIONS

Paul, William, Fundamental Immunology, 3rd Edition, Raven Press, New York, 1993, pp. 292-295.*
Rudikoff et al., Single amino acid substitution altering antigen-binding specificity. Proc. Natl. Acad. Sci. USA 79:1979-1983, 1982.*
Vajdos et al., Comprehensive functional maps of the antigen-binding site of an anti-ErbB2 antibody obtained with shotgun scanning mutagenesis. J. Mol. Biol. 320:415-428, 2002.*
International Search Report mailed Sep. 26, 2011 (PCT/EP20111060819); ISA/EP.
Carter et al., "Potent Antibody Therapeutics by Design," Nature Reviews, Immunology, vol. 6, 2006, pp. 343-357.
Davies et al., "Affinity improvement of single antibody VH domains: residues in all three hypervariable regions affect antigen binding," Immunotechnology, vol. 2, No. 3, 1996, pp. 169-179.
Holt et al., "Domain antibodies: proteins for therapy," Trends in Biotechnology, vol. 21, No. 11, 2003, pp. 484-490.
Porunelloor et al. "The LLT1 receptor induces IFN-gamma production by human natural killer cells," Molecular Immunology, 2004, vol. 40, No. 16, pp. 1157-1163.
Rosen et al., "Cutting edge: lectin-like transcript-1 is a ligand for the inhibitory human NKR-P1A receptor," The Journal of Immunology, 2005, vol. 175, No. 12, 2005, pp. 7796-7799.
Rosen et al., "Functional consequences of interactions between human NKR-P1A and its ligand LLT1 expressed on activated dendritic cells and B cells," The Journal of Immunology, 2008, vol. 180, No. 10, pp. 6508-6517.
Roth et al., "Malignant glioma cells counteract antitumor immune responses through expression of lectin-like transcript-1," Cancer Research, 2007: vol. 67, No. 8, 2007, pp. 3540-3544.
Wark et al., "Latest technologies for the enhancement of antibody affinity," Advanced Drug Delivery Reviews, vol. 58, Nos. 5-6, 2006, pp. 657-670.
Rajpal et al., "A general method for greatly improving the affinity of antibodies by using combinatorial libraries," PNAS, Jun. 14, 2005, vol. 102, No. 24, pp. 8466-8471.

* cited by examiner

*Primary Examiner* — Ruixiang Li
(74) *Attorney, Agent, or Firm* — Banner & Witcoff, Ltd.

(57) ABSTRACT

The present invention relates to monoclonal antibodies that are capable of specifically binding to lectin-like transcript 1 (LLT1), to polynucleotides encoding such antibodies and to cells that express such antibodies. Antibodies of the invention have utility in the treatment of autoimmune diseases and cancer, in which LLT1-and CD161-expressing cells play a role in disease pathogenesis.

4 Claims, 14 Drawing Sheets

Fig. 1

```
Heavy Chain
         1         2         3         4         5         6
1234567890123456789012345678912345AB67890123456789012ABC34567890
EVQLVESGGGLVQPGGSLKLSCAASGFTVSSYGMS  WVRQIPDKRLELVATINS  NGGRTFYP 4F68
EVQLVESGGDLVKPGGSLKLSCAASGFTFSSYGMS  WVRQTPDKRLEWVATISS  GGSYTYYP 3:3.9

7         8         9        10                 11
12345678901234567890123ABC345678901234567890ABCDEFGHIJK1234567890 <- Kabat
DSVKGRFTISRDNAQNTLYLQMSSLKSEDTAMYYCARDGGYWAHF        DYWGQGTTLTVSS 4F68
DSVKGRFTISRDNAKNTLYLQMSSLKSEDTAMYYCAR/    /YF        DYWGQGTTLTVSS
3:3.9//JH2

Light Chain
         1         2         3         4         5         6
1234567890123456789012344567ABCDEF890123456789012345678901234567890
DVLMTQTPLSLPVSLGDQASISCRSSQSIVHS NGNTYLEWYLQKPGQSPKLLIYKVSNRFSGVPD 4F68
DVLMTQTPLSLPVSLGDQASISCRSSQSIVHS NGNTYLEWYLQKPGQSPKLLIYKVSNRFSGVPD cr1

7         8         9        10
12345678901234567890123456789012345AB67890123456789 <- The Kabat Scheme
RFSGSGSGTDFTLKISRVEAEDLGVYYCFQGSHVP  WTFGGGTKLEIKR 4F68
RFSGSGSGTDFTLKISRVEAEDLGVYYCFQGSHVP//WTFGGGTKLEIKR cr1/JK1
```

Fig. 2

```
Heavy Chain
         1         2         3           4         5         6
1234567890123456789012345678901234 5AB67890123456789012ABC34567890
EVQLQQSGAELVRSGASVKLSCTASGFNIKDYYMH    WVKQRPEQGLEWIGWIDP    ENGDTEYA  2F1
EVQLQXSVAELXXXGASVKLSCTASGFNIKNTYMH    WVKQRPEQGLEWIGRIDP    ANGNTKYA  V130

7         8         9         10                 11
12345678901234567890 12ABC345678901234567890ABCDEFGHIJK1234567890  <- Kabat
PKFQGKATVTADTSSNTVYLQLSSLTSEDTAVYYCNGEIITTTAWF          TYWGQGTLVTVSA  2F1
PKFQXKATITADTSSNTAYLQLSSLTSEDTAIYYC/    /AWF            AYWGQGTLVTVSA
V130//JH3

Light Chain
         1         2         3           4         5         6
123456789012345678901234 4567ABCDEF890123456789012345678901234567890
DIVMTQTPISLSVTIGQPASISCKSSQSLLYTNGKTYLNWLLQRPGQSPKRLIYLVSKLDSGVPD  2F1
DVVMTQTPLTLSVTIGQPASISCKSSQSLLYSNGKTYLNWLLQRPGQSPKRLIYLVSKLDSGVPD  bj2

7         8         9         10
1234567890123456789012345678 9012345AB67890123456789  <- The Kabat Scheme
RFSGSGSGTDFTLKISRVEAEDLGVYYCLQNTHFP   HTFGGGTKLEIKR  2F1
RFTGSGSGTDFTLKISRVEAEDLGVYYCVQGTHFP//YTFGGGTKLEIKR  bj2/JK2
```

Fig. 5
A)
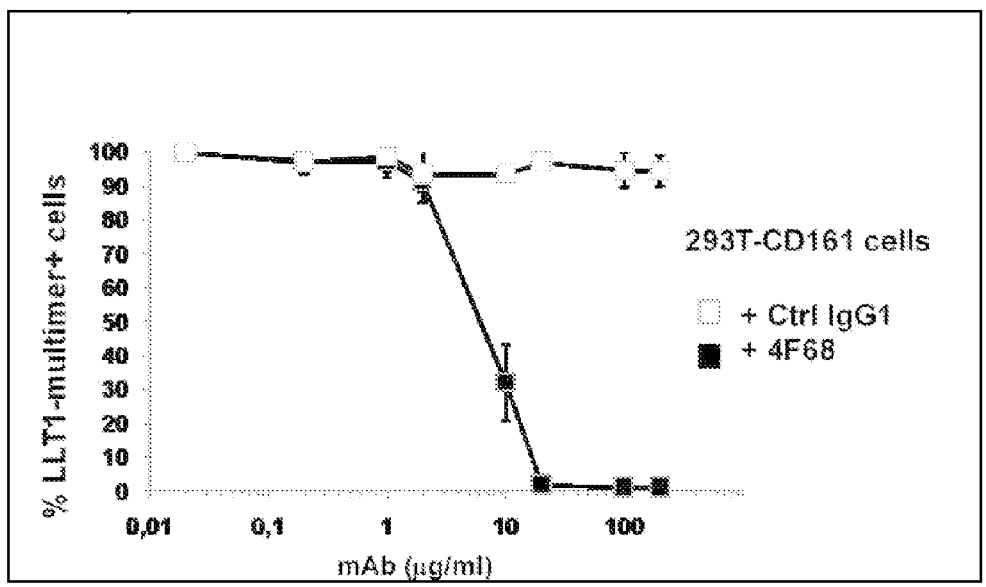
B)
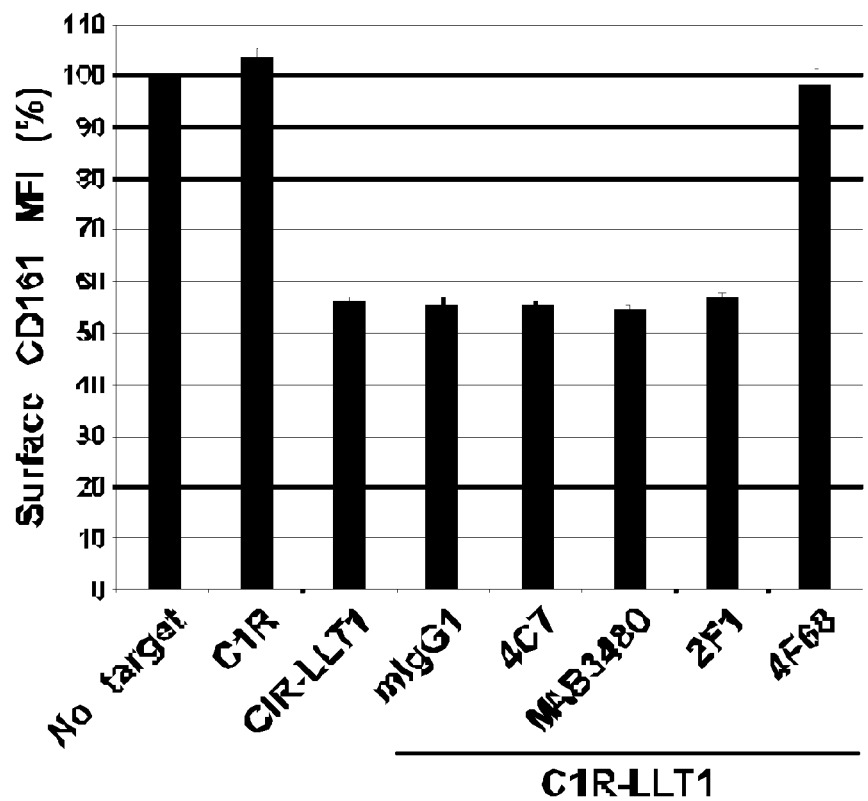

Fig. 8
A)
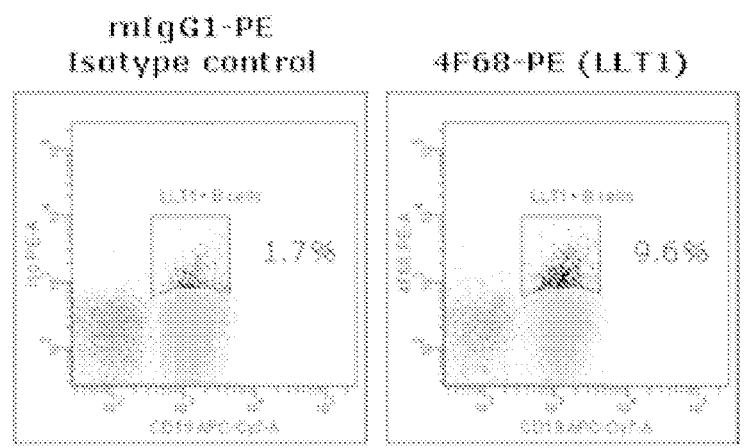
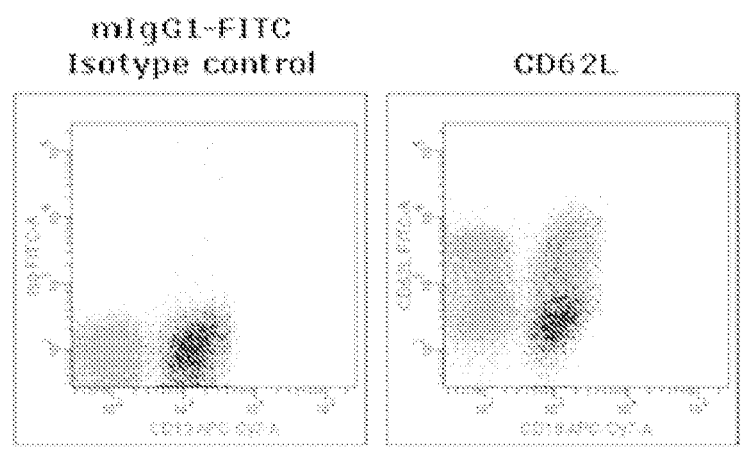
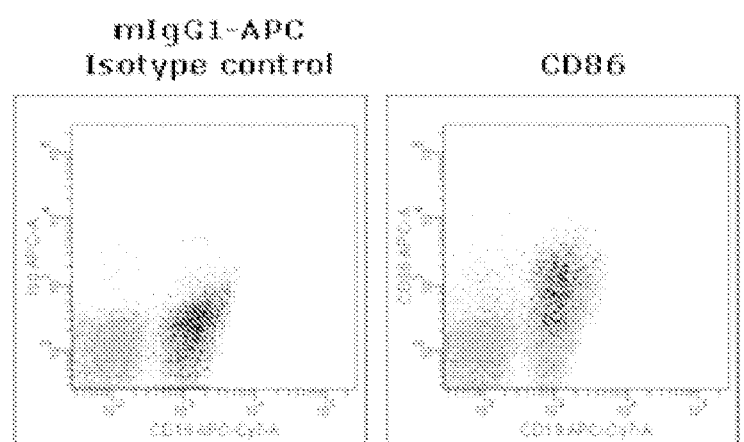

Fig. 8 (cont.)
B)
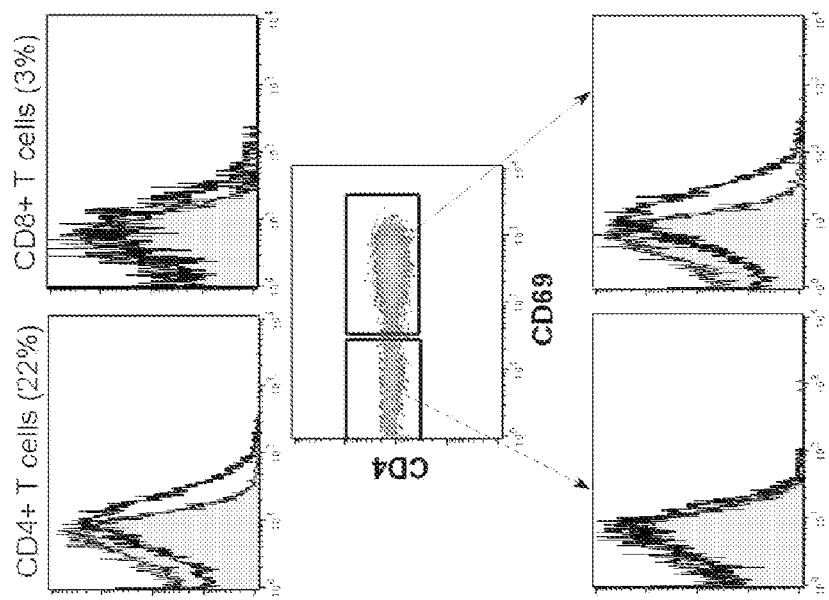
C)
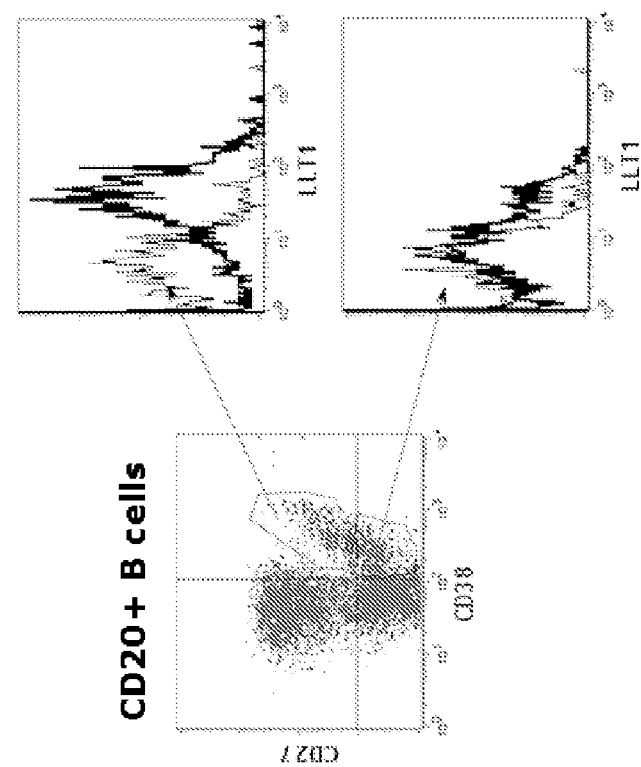

A)

B)

C)

SEQUENCE LISTING

<160> NUMBER OF SEQ ID NOS: 13

<210> SEQ ID NO 1
<211> LENGTH: 191
<212> TYPE: PRT
<213> ORGANISM: Homo sapiens

<400> SEQUENCE: 1

Met His Asp Ser Asn Asn Val Glu Lys Asp Ile Thr Pro Ser Glu Leu
1               5                   10                  15

Pro Ala Asn Pro Gly Cys Leu His Ser Lys Glu His Ser Ile Lys Ala
            20                  25                  30

Thr Leu Ile Trp Arg Leu Phe Phe Leu Ile Met Phe Leu Thr Ile Ile
        35                  40                  45

Val Cys Gly Met Val Ala Ala Leu Ser Ala Ile Arg Ala Asn Cys His
    50                  55                  60

Gln Glu Pro Ser Val Cys Leu Gln Ala Ala Cys Pro Glu Ser Trp Ile
65                  70                  75                  80

Gly Phe Gln Arg Lys Cys Phe Tyr Phe Ser Asp Asp Thr Lys Asn Trp
                85                  90                  95

Thr Ser Ser Gln Arg Phe Cys Asp Ser Gln Asp Ala Asp Leu Ala Gln
            100                 105                 110

Val Glu Ser Phe Gln Glu Leu Asn Phe Leu Arg Tyr Lys Gly Pro
        115                 120                 125

Ser Asp His Trp Ile Gly Leu Ser Arg Glu Gln Gly Gln Pro Trp Lys
    130                 135                 140

Trp Ile Asn Gly Thr Glu Trp Thr Arg Gln Phe Pro Ile Leu Gly Ala
145                 150                 155                 160

Gly Glu Cys Ala Tyr Leu Asn Asp Lys Gly Ala Ser Ser Ala Arg His
                165                 170                 175

Tyr Thr Glu Arg Lys Trp Ile Cys Ser Lys Ser Asp Ile His Val
            180                 185                 190

<210> SEQ ID NO 2
<211> LENGTH: 357
<212> TYPE: DNA
<213> ORGANISM: Artificial
<220> FEATURE:
<223> OTHER INFORMATION: Heavy chain variable domain (VH) of anti-
      LLT14F68

<400> SEQUENCE: 2
gaggtgcagc tggtggagtc tgggggaggc ttagtgcagc ctggagggtc cctgaaactc      60
tcctgcgcag cctctggatt cactgtcagt agctatggca tgtcttgggt tcgccagatt     120
ccagacaaga ggctggagtt ggtcgcaacc attaatagta atggtggtag gaccttttat     180
ccagacagtg tgaagggccg attcaccatc tccagagaca tgcccagaa caccctgtac      240 ctgcaaatga gcagtctgaa gtctgaggac acagccatgt attactgtgc aagagatggg     300
gggtactggg cccactttga ctactggggc caaggcacca ctctcacagt ctcctca       357

<210> SEQ ID NO 3
<211> LENGTH: 357
<212> TYPE: DNA
<213> ORGANISM: Artificial
<220> FEATURE:
<223> OTHER INFORMATION: Heavy chain variable domain (VH) of anti-
      LLT14F68

<400> SEQUENCE: 3

```
ctccacgtcg accacctcag accccctccg aatcacgtcg acctcccag ggactttgag      60 aggacgcgtc ggagacctaa gtgacagtca tcgataccgt acagaaccca agcggtctaa    120
ggtctgttct ccgacctcaa ccagcgttgg taattatcat taccaccatc ctggaaaata    180
ggtctgtcac acttcccggc taagtggtag aggtctctgt tacgggtctt gtgggacatg    240
gacgtttact cgtcagactt cagactcctg tgtcggtaca taatgacacg ttctctaccc    300
cccatgaccc gggtgaaact gatgaccccg gttccgtggt gagagtgtca gaggagt       357
```

<210> SEQ ID NO 4
<211> LENGTH: 119
<212> TYPE: PRT
<213> ORGANISM: Artificial
<220> FEATURE:
<223> OTHER INFORMATION: Heavy chain variable domain (VH) of anti-
      LLT14F68

<400> SEQUENCE: 4

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Val Ser Ser Tyr
            20                  25                  30

Gly Met Ser Trp Val Arg Gln Ile Pro Asp Lys Arg Leu Glu Leu Val
        35                  40                  45

Ala Thr Ile Asn Ser Asn Gly Gly Arg Thr Phe Tyr Pro Asp Ser Val
    50                  55                  60

Lys Gly Arg Phe Thr Ile Ser Arg Asp Asn Ala Gln Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Asp Gly Gly Tyr Trp Ala His Phe Asp Tyr Trp Gly Gln Gly
            100                 105                 110

Thr Thr Leu Thr Val Ser Ser
        115
```

<210> SEQ ID NO 5
<211> LENGTH: 339
<212> TYPE: DNA
<213> ORGANISM: Artificial
<220> FEATURE:
<223> OTHER INFORMATION: Light chain variable domain (VL) of anti-
      LLT14F68

<400> SEQUENCE: 5

```
gatgttttga tgacccaaac tccactctcc ctgcctgtca gtcttggaga tcaagcctcc     60
atctcttgca gatctagtca gagcattgta catagtaatg aaacaccta tttagaatgg    120 tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttccg    300
tggacgttcg gtggaggcac caagctggaa atcaaacgg                          339
```

<210> SEQ ID NO 6
<211> LENGTH: 339
<212> TYPE: DNA
<213> ORGANISM: Artificial
<220> FEATURE:
<223> OTHER INFORMATION: Light chain variable domain (VL) of anti-
      LLT14F68

<400> SEQUENCE: 6

```
ctacaaaact actgggtttg aggtgagagg gacggacagt cagaacctct agttcggagg    60
tagagaacgt ctagatcagt ctcgtaacat gtatcattac ctttgtggat aaatcttacc   120
atggacgtct ttggtccggt cagaggtttc gaggactaga tgtttcaaag gttggctaaa   180
agacccagg gtctgtccaa gtcaccgtca cctagtccct gtctaaagtg tgagttctag    240
tcgtctcacc tccgactcct agaccctcaa ataatgacga agttccaag tgtacaaggc    300
acctgcaagc cacctccgtg gttcgacctt tagtttgcc                          339
```

<210> SEQ ID NO 7
<211> LENGTH: 113
<212> TYPE: PRT
<213> ORGANISM: Artificial
<220> FEATURE:
<223> OTHER INFORMATION: Light chain variable domain (VL) of anti-LLT14F68

<400> SEQUENCE: 7

```
Asp Val Leu Met Thr Gln Thr Pro Leu Ser Leu Pro Val Ser Leu Gly
1               5                   10                  15
Asp Gln Ala Ser Ile Ser Cys Arg Ser Ser Gln Ser Ile Val His Ser
            20                  25                  30
Asn Gly Asn Thr Tyr Leu Glu Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Tyr Cys Phe Gln Gly
                85                  90                  95
Ser His Val Pro Trp Thr Phe Gly Gly Gly Thr Lys Leu Glu Ile Lys
            100                 105                 110
Arg
```

<210> SEQ ID NO 8
<211> LENGTH: 360
<212> TYPE: DNA
<213> ORGANISM: Artificial
<220> FEATURE:
<223> OTHER INFORMATION: Heavy chain variable domain (VH) of anti-LLT12F1A5

<400> SEQUENCE: 8

```
gaggttcagc tgcagcagtc tggggcagag cttgtgaggt caggggcctc agtcaagttg    60
tcctgcacag cttctggctt caacattaaa gactactata tgcactgggt gaagcagagg   120
cctgaacagg gcctggagtg gattggatgg attgatcctg agaatggtga tactgaatat   180
gccccgaagt tccagggcaa ggccactgtg actgcagaca catcctccaa cacagtctac   240
ctgcagctca gcagcctgac atctgaggac actgccgtct attactgtaa tggagagatt   300
attacgacta ctgcctggtt tacttactgg ggccaaggga ctctggtcac tgtctctgca   360
```

<210> SEQ ID NO 9
<211> LENGTH: 360
<212> TYPE: DNA
<213> ORGANISM: Artificial
<220> FEATURE:
<223> OTHER INFORMATION: Heavy chain variable domain (VH) of anti-

LLT12F1A5

<400> SEQUENCE: 9

```
ctccaagtcg acgtcgtcag accccgtctc gaacactcca gtccccggag tcagttcaac    60
aggacgtgtc gaagaccgaa gttgtaattt ctgatgatat acgtgaccca cttcgtctcc   120
ggacttgtcc cggacctcac ctaacctacc taactaggac tcttaccact atgacttata   180
cggggcttca aggtcccgtt ccggtgacac tgacgtctgt gtaggaggtt gtgtcagatg   240
gacgtcgagt cgtcggactg tagactcctg tgacggcaga atgacatt acctctctaa     300
taatgctgat gacggaccaa atgaatgacc ccggttccct gagaccagtg acagagacgt   360
```

<210> SEQ ID NO 10
<211> LENGTH: 120
<212> TYPE: PRT
<213> ORGANISM: Artificial
<220> FEATURE:
<223> OTHER INFORMATION: Heavy chain variable domain (VH) of anti-LLT12F1A5

<400> SEQUENCE: 10

```
Glu Val Gln Leu Gln Gln Ser Gly Ala Glu Leu Val Arg Ser Gly Ala
1               5                   10                  15
Ser Val Lys Leu Ser Cys Thr Ala Ser Gly Phe Asn Ile Lys Asp Tyr
            20                  25                  30
Tyr Met His Trp Val Lys Gln Arg Pro Glu Gln Gly Leu Glu Trp Ile
        35                  40                  45
Gly Trp Ile Asp Pro Glu Asn Gly Asp Thr Glu Tyr Ala Pro Lys Phe
    50                  55                  60
Gln Gly Lys Ala Thr Val Thr Ala Asp Thr Ser Ser Asn Thr Val Tyr
65                  70                  75                  80
Leu Gln Leu Ser Ser Leu Thr Ser Glu Asp Thr Ala Val Tyr Tyr Cys
                85                  90                  95
Asn Gly Glu Ile Ile Thr Thr Thr Ala Trp Phe Thr Tyr Trp Gly Gln
            100                 105                 110
Gly Thr Leu Val Thr Val Ser Ala
        115                 120
```

<210> SEQ ID NO 11
<211> LENGTH: 339
<212> TYPE: DNA
<213> ORGANISM: Artificial
<220> FEATURE:
<223> OTHER INFORMATION: Light chain variable domain (VL) of anti-LLT12F1A5

<400> SEQUENCE: 11

```
gatattgtga tgacccagac tccaatcagt ttgtcggtta ccattggaca accagcttcc    60
atctcttgca gtcaagtca gagcctctta tatactaatg aaaaaccta tttgaattgg    120
ttattacaga ggccaggcca gtctccaaaa cgcctaatct atctggtgtc taaattggac   180
tctggagtcc ctgacaggtt cagtggcagt ggatcaggga cagatttcac actgaaaatc   240
agcagagtgg aggctgagga tttgggagtt tattactgct tgcagaatac acattttcct   300
cacacgttcg gaggggggac caagctggaa ataaaacgg                          339
```

<210> SEQ ID NO 12
<211> LENGTH: 339
<212> TYPE: DNA
<213> ORGANISM: Artificial

```
<220> FEATURE:
<223> OTHER INFORMATION: Light chain variable domain (VL) of anti-
      LLT12F1A5

<400> SEQUENCE: 12
ctataacact actgggtctg aggttagtca aacagccaat ggtaacctgt tggtcgaagg      60
tagagaacgt tcagttcagt ctcggagaat atatgattac cttttggat aaacttaacc     120 aataatgtct ccggtccggt cagaggtttt gcggattaga tagaccacag atttaacctg    180
agacctcagg gactgtccaa gtcaccgtca cctagtccct gtctaaagtg tgacttttag    240
tcgtctcacc tccgactcct aaaccctcaa ataatgacga acgtcttatg tgtaaaagga    300
gtgtgcaagc ctcccccctg gttcgacctt tattttgcc                            339

<210> SEQ ID NO 13
<211> LENGTH: 113
<212> TYPE: PRT
<213> ORGANISM: Artificial
<220> FEATURE:
<223> OTHER INFORMATION: Light chain variable domain (VL) of anti-
      LLT12F1A5

<400> SEQUENCE: 13

Asp Ile Val Met Thr Gln Thr Pro Ile Ser Leu Ser Val Thr Ile Gly
1               5                   10                  15

Gln Pro Ala Ser Ile Ser Cys Lys Ser Ser Gln Ser Leu Leu Tyr Thr
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Asn
                85                  90                  95

Thr His Phe Pro His Thr Phe Gly Gly Gly Thr Lys Leu Glu Ile Lys
            100                 105                 110

Arg
```

LLT-1 ANTIBODIES WITH NEW FUNCTIONAL PROPERTIES

The present application is a U.S. National Phase filing of International Application No. PCT/EP2011/060819, filed on Jun. 28, 2011, designating the United States of America and claiming priority to European Patent Application No. 10167668.2, filed on Jun. 29, 2010; U.S. Patent Application No. 61/360,520, filed on Jul. 1, 2010; European Patent Application No. 10168095.7, filed on Jul. 1, 2010; U.S. Patent Application No. 61/362,319, filed on Jul. 8, 2010; European Patent Application No. 10169409.9, filed on Jul. 13, 2010 and U.S. Patent Application No. 61/364,156, filed on Jul. 14, 2010. The present application claims priority to and the benefit of the above-identified applications, and each of the above-identified applications is incorporated by reference herein in its entirety.

FIELD OF THE INVENTION

The present invention relates to monoclonal antibodies that are capable of specifically binding to lectin-like transcript 1 (LLT1), also known as C-type lectin domain family 2 member D (CLEC2D).

BACKGROUND OF THE INVENTION

LLT1 is expressed on the surface of activated immune cells, such as B, T, NK and dendritic cells, but is absent from resting, naïve cells. The receptor for LLT1 is CD161, also known as NKRP1A. CD161 is found on NK cells and effector/memory T cells. In T cells, the CD161 receptor functions as a co-stimulator of TCR signalling, whereas in NK cells CD161 is a cytotoxicity inhibitory receptor that restricts killing of cells expressing the CD161-ligand, LLT1.

In chronic autoimmune diseases such as inflammatory bowel diseases (ulcerative colitis and Crohn's disease), LLT1 expression is increased due to its presence on subsets of infiltrating inflammatory immune cells. CD161+ T cells home to the intestine and are markedly up-regulated, in number, in inflamed tissue from patients with Crohn's disease. Certain lymphomas, such as follicular lymphomas, are also characterized by LLT1 expression.

Several anti-LLT1 monoclonal antibodies have been described in the literature and/or are commercial available. One of these, L9.7, was reported to bind specifically to LLT1 and to induce IFNγ secretion by NK cells without affecting the cytotoxic response (Mathew et al, 2004). Rosen et al (2008) describes two murine anti-LLT1 monoclonal antibodies, 402624 and 402659 (the latter is now commercially available via R&D Systems, product No. MAB3480). Roth et al (2007) describes the murine anti-LLT1 monoclonal antibody 4C7. None of these three antibodies block the interaction between LLT1 and CD161.

Biological therapeutics are now available for the treatment of certain autoimmune diseases and/or cancer. For example, patients with cancer may be treated with anti-CD20; patients with rheumatoid arthritis may be treated with anti-CD20, a TNF-R antagonist or anti-TNF-α; patients with psoriasis may be treated with anti-CD11a; patients with multiple sclerosis may be treated with INF-γ; patients with ulcerative colitis may be treated with TNF-α and patients with Crohn's disease may be treated with Infliximab or Natalizumab. Unfortunately, patients that receive treatment with any one of these biologicals also experience a variety of dramatic side-effects and/or are non-responders and/or develop inhibitors. There is still a need for alternative biological medicaments which specifically target pathological tissue and/or which do not affect healthy tissue and/or which result in less severe side effects, and/or which result in fewer side effects, and/or which may be used long-term and/or which do not result in the formation of inhibitors. The current invention relates to these unmet needs amongst patients with cancer, and in those with autoimmune diseases and in those with chronic inflammatory diseases.

SUMMARY OF THE INVENTION

The invention relates to monoclonal antibodies that are capable of specifically binding to lectin-like transcript 1 (LLT1) and which modulate the function of LLT1- and CD161-bearing, normal and abnormal cells. Antibodies of the invention may block the interaction between LLT1 and CD161, thereby stimulating, for example, the cytokine production and the cytotoxicity of NK cells. Antibodies according to the invention may facilitate the removal of LLT1-expressing cells by antibody-dependent cell-mediated cytotoxicity (ADCC) and/or by complement-dependent cytotoxicity (CDC). Binding affinities of these antibodies for LLT1 are typically in the range of $1 \times 10^{-8}$M or less and is, preferably, at least 2-fold less than that with which they bind to other lectins of the C-type lectin superfamily. Other, as yet unidentified monoclonal antibodies which, in binding to LLT1, compete with the monoclonal antibodies that are specifically disclosed herein are also antibodies according to the current invention.

The invention also relates to nucleic acid constructs that encode monoclonal antibodies capable of specifically binding LLT1, as well as to isolated cells that comprise such nucleic acid constructs, or that express the monoclonal antibodies of the invention.

These monoclonal antibodies may be formulated and used to treat a subject that has an autoimmune disease and/or a chronic inflammatory disease and/or cancer. A method of treating an autoimmune disease and/or a chronic inflammatory disease and/or cancer comprises administering a therapeutically or prophylactically effective amount of such a monoclonal antibody to a subject in need thereof.

DESCRIPTION OF THE SEQUENCES

SEQ ID NO: 1 provides the polypeptide sequence of human LLT1.

SEQ ID NOs: 2-4 provide the polynucleotide (sense and antisense) and polypeptide sequences of the heavy chain variable domain (VH) of anti-LLT14F68.

SEQ ID NOs: 5-7 provide the polynucleotide (sense and antisense) and polypeptide sequences of the light chain variable domain (VL) of anti-LLT14F68.

SEQ ID NOs: 8-10 provide the polynucleotide (sense and antisense) and polypeptide sequences of the heavy chain variable domain (VH) of anti-LLT12F1A5.

SEQ ID NOs: 11-13 provide the polynucleotide (sense and antisense) and polypeptide sequences of the light chain variable domain (VL) of anti-LLT12F1A5.

DESCRIPTION OF THE DRAWINGS

FIG. 1 shows the amino acid sequences of the heavy chain (HC) and light chain (LC) CDRs of the monoclonal antibody, anti-LLT14F.

FIG. 2 shows the amino acid sequences of the heavy chain (HC) and light chain (LC) CDRs of the monoclonal antibody, anti-LLT12F1A5.

FIG. 5 shows that anti-LLT14F, blocks binding of LLT1-Fc multimers to CD161 transfectants and that anti-LLT14F but not 2F1A5, MAB3480 and 4C7 blocks LLT1-induced downregulation of CD161 on NK cells incubated with LLT1-expressing cells.

FIG. 8 shows that LLT1 is expressed on subsets of B and T lymphocytes in the tonsillar tissue of individuals with tonsillitis, as valuated by means of flow cytometry.

DESCRIPTION OF THE INVENTION

Figure 3:
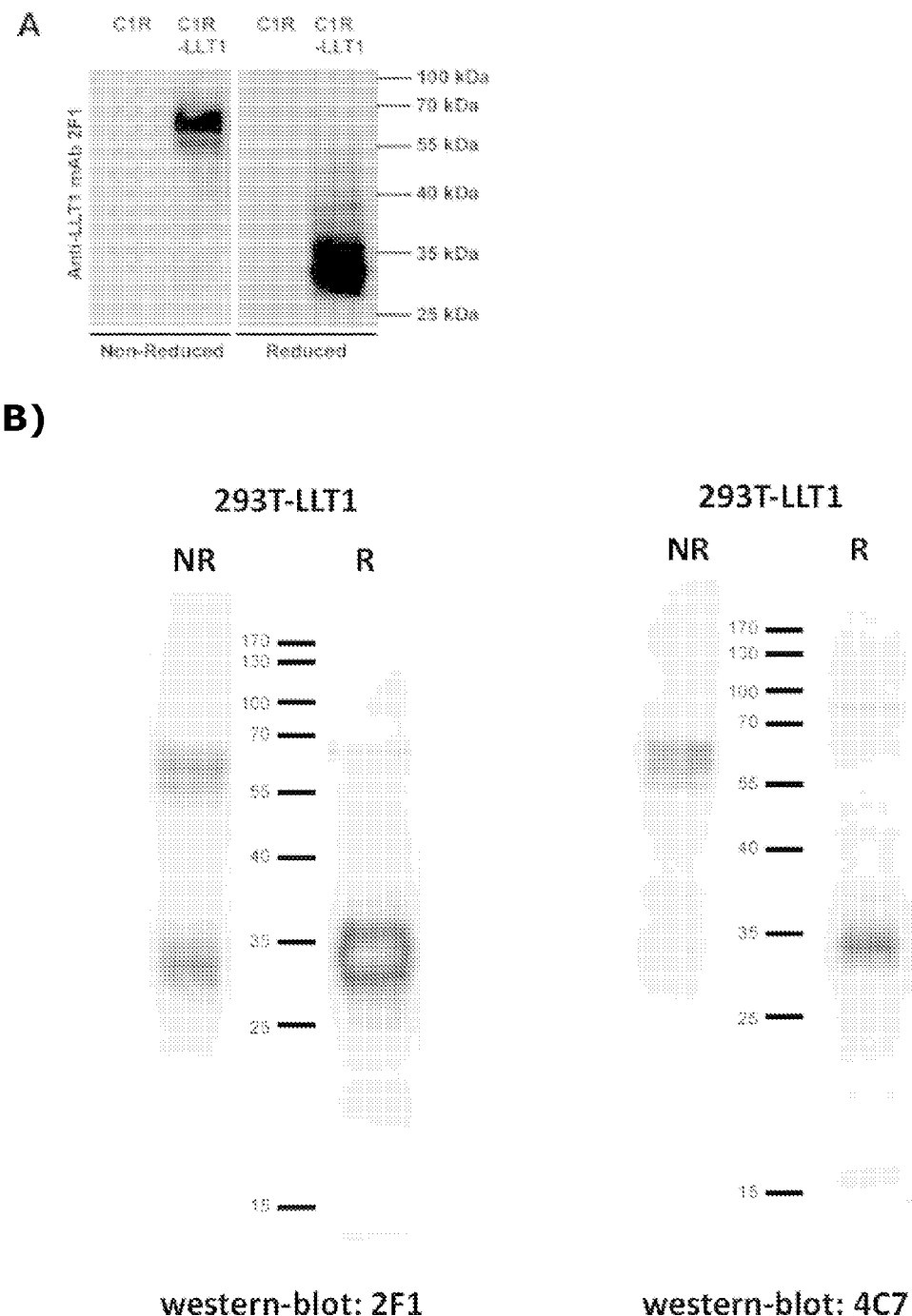
FIG. 3 Characterization of recombinant LLT1 expressed by C1R and HEK-293T cells.

The present invention relates to antibodies that are capable of binding to lectin-like transcript 1 (LLT1). The antibodies may be capable of specifically binding LLT1.

Preferred antibodies are those that bind to LLT1 and that do not bind other molecules, or that bind other molecules with a lower affinity than LLT1. In particular, the invention relates to antibodies that bind to LLT1 and that modulate the activity of cells that LLT1 is expressed upon, or that express LLT1's co-receptor, CD161. Antibodies of the invention may thus possess the ability to modulate the immune system. The invention also relates to uses for such antibodies, such as therapeutic and pharmaceutical uses.

The term "LLT1", as used herein, encompasses any naturally occurring form of LLT1 which may be derived from any suitable organism. For example, LLT1 for use as described herein may be vertebrate LLT1, such as mammalian LLT1, such as LLT1 from a primate (such as a human); a rodent (such as a mouse or a rat), a lagomorph (such as a rabbit), or an artiodactyl (such a cow, sheep, pig or camel). Preferably, the LLT1 is human LLT1. The LLT1 may be a mature form of LLT1 such as an LLT1 protein that has undergone post-translational processing within a suitable cell. The LLT1 may be a full length LLT1 protein. The LLT1 may be a variant, an isoform or another homolog of an LLT1 molecule. Variant LLT1 molecules are generally characterised by having the same type of activity as naturally occurring LLT1, such as the ability to bind CD161.

An antibody of the invention may be a monoclonal antibody or a polyclonal antibody. For the production of both monoclonal and polyclonal antibodies, the experimental animal is a suitable mammal such as, but not restricted to, a goat, rabbit, rat or mouse. In one embodiment, an antibody of the invention is a monoclonal antibody.

Monoclonal antibodies are immunoglobulin molecules that are identical to each other and have a single binding specificity and affinity for a particular epitope. Monoclonal antibodies (mAbs) of the present invention can be produced by a variety of techniques, including conventional monoclonal antibody methodology e.g., the standard somatic cell hybridization technique of Kohler and Milstein (1975) Nature 256: 495, or viral or oncogenic transformation of B lymphocytes. The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

To generate hybridomas that produce monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. The antibody secreting hybridomas can be re-plated, screened again, and if still positive for suitable IgG, the hybridomas can be subcloned at least twice by limiting dilution. The stable subclones can then be cultured in vitro to generate small amounts of antibody in tissue culture medium for characterization.

An antibody of the invention may be prepared, expressed, created or isolated by recombinant means, such as (a) antibodies isolated from an animal (e.g., a mouse) that is transgenic or transchromosomal for the immunoglobulin genes of interest or a hybridoma prepared therefrom, (b) antibodies isolated from a host cell transformed to express the antibody of interest, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "antibody", as referred to herein, includes whole antibodies and any antigen binding fragment (i.e., "antigen-binding portion") or single chains thereof. An antibody refers to a glycoprotein comprising at least two heavy chains (HC) and two light chains (LC) inter-connected by disulfide bonds, or an antigen binding portion thereof. Each heavy chain is comprised of a heavy chain variable region (abbreviated herein as VH) and a heavy chain constant region (CH). Each light chain is comprised of a light chain variable region (abbreviated herein as VL) and a light chain constant region (CL). The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

As used herein, the term Ab comprises an antibody, or a fragment thereof, which specifically binds its corresponding antigen (Ag). Examples of antigen-binding fragments include Fab, Fab', F(ab)2, F(ab')2, F(ab)S, Fv (typically the VL and VH domains of a single arm of an antibody), single-chain Fv (scFv; see e.g. Bird et al., Science 1988; 242:42 S-426; and Huston et al. PNAS 1988; 85:5879-5883), dsFv, Fd (typically the VH and CHI domain), and dAb (typically a VH domain) fragments; VH, VL, VhH, and V-NAR domains; monovalent molecules comprising a single VH and a single VL chain; minibodies, diabodies, triabodies, tetrabodies, and kappa bodies (see, e.g., Ill et al. Protein Eng 1997; 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 2S:1126-1136; WO2005040219, and published U.S. Patent Applications 20050238646 and 20020161201.

Antibody fragments can be obtained using conventional recombinant or protein engineering techniques, and the fragments can be screened for binding to LLT1, or another function, in the same manner as intact antibodies.

Antibody "fragments" of the invention may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions.

An antibody of the invention may be, or may comprise, a fragment of the anti-LLT14F68 antibody, or a variant thereof, or the anti-LLT2F1A5 antibody, or a variant thereof. The antibody of the invention may be, or may comprise, an antigen binding portion of this antibody or a variant thereof as discussed further above. For example, the antibody of the invention may be a Fab fragment of one of these antibodies or variants thereof, or it may be a single chain antibody derived from one of these antibodies, or a variant thereof.

An antibody of the invention may be a human antibody or a humanised antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Such a human antibody may be a human monoclonal antibody. Such a human monoclonal antibody may be produced by a hybridoma which includes a B cell obtained from a transgenic nonhuman animal, e.g., a transgenic mouse, having a genome comprising a human heavy chain transgene and a light chain transgene fused to an immortalized cell.

Human antibodies may be isolated from sequence libraries built on selections of human germline sequences further diversified with natural and synthetic sequence diversity.

Human antibodies may be prepared by in vitro immunisation of human lymphocytes followed by transformation of the lymphocytes with Epstein-Barr virus.

The term "human antibody derivatives" refers to any modified form of the human antibody, e.g., a conjugate of the antibody and another agent or antibody.

The term "humanized antibody" is intended to refer to a human/non-human chimeric antibody that contains a minimal sequence (CDR regions) derived from non-human immunoglobulin. Humanized antibodies are thus human immunoglobulins (recipient antibody) in which residues from a hyper-variable region of the recipient are replaced by residues from a hypervariable region of a non-human species (donor antibody) such as mouse, rat, rabbit, or non-human primate having the desired specificity, affinity, and capacity. In some instances, FR residues of the human immunoglobulin are replaced by corresponding non-human residues. An example of such a modification is the introduction of one or more so-called back-mutations.

Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin.

In another aspect, the present invention features multi-specific molecules comprising an anti-LLT1 antibody, or an antigen-fragment thereof, of the invention. Such multi-specific molecules include bispecific molecules comprising at least one first binding specificity for LLT1 and a second binding specificity for a second target epitope. One type of bispecific molecules are bispecific antibodies as known in the art. Bispecific antibodies, or indeed multi-specific antibodies, may be prepared as full-length antibodies or antibody fragments (e.g. F(ab')2 bispecific antibodies) or any other antigen-binding fragments described herein.

In one aspect, the present invention features antibody derivatives (or immunoconjugates), such as anti-LLT1 antibodies conjugated or covalently bound to a second agent. The second agent can be linked to the antibody directly or indirectly, using any of a large number of available methods known to the person skilled in the art. For example, an agent can be attached at the hinge region of the reduced antibody component via disulfide bond formation, using cross-linkers such as N-succinyl S-(2-pyridyldithio) proprionate (SPDP), or via a carbohydrate moiety in the Fc region of the antibody.

In one aspect, antibodies of the invention may be engineered to include modifications within the Fc region, typically to alter one or more functional properties of the antibody, such as serum half-life, complement fixation, Fc receptor binding, protein stability and/or antigen-dependent cellular cytotoxicity, or lack thereof. Furthermore, an antibody of the invention may be chemically modified (e.g., one or more chemical moieties can be attached to the antibody) or be modified to alter its glycosylation, again to alter one or more functional properties of the antibody.

The isotype of an antibody of the invention may be IgG, such as IgG1, such as IgG2, such as IgG4. If desired, the class of an antibody may be "switched" by known techniques. For example, an antibody that was originally produced as an IgM molecule may be class switched to an IgG antibody. Class switching techniques also may be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed.

In one embodiment, the hinge region of CHI is modified such that the number of cysteine residues in the hinge region is altered, e.g., increased or decreased. This approach is described further for instance in U.S. Pat. No. 5,677,425 by Bodmer et al.

The constant region may further be modified to stabilize the antibody, e.g., to reduce the risk of a bivalent antibody separating into two monovalent VH-VL fragments. For example, in an IgG4 constant region, residue S241 may be mutated to a proline (P) residue to allow complete disulphide bridge formation at the hinge (see, e.g., Angal et al., Mol. Immunol. 199S; 30:105-8).

The term "antigen" (Ag) refers to the molecular entity used for immunization of an immunocompetent vertebrate to produce the antibody (Ab) that recognizes the Ag. Herein, Ag is termed more broadly and is generally intended to include target molecules that are specifically recognized by the Ab, thus including fragments or mimics of the molecule used in the immunization process for raising the Ab. Thus, for Ab's binding to LLT1: both isolated full-length LLT1 and truncated or other variants of LLT1 are referred to as an Ag.

The strength of the non-covalent, monovalent interactions between antibodies of the invention and LLT1 may be defined in terms of binding affinity. Binding affinity may be quantified by determining the dissociation constant ($K_D$). In turn, $K_D$ can be determined by measurement of the kinetics of complex formation and dissociation. The rate constants corresponding to the association and the dissociation of a monovalent complex are referred to as the association rate constants $k_a$ (or $k_{on}$) and dissociation rate constant $k_d$ (or $k_{off}$), respectively. $K_D$ is related to $k_a$ and $k_d$ through the equation $K_D = k_d/k_a$.

Following this definition, binding affinities that are associated with different antibody/LLT1 interactions may be compared by comparison of the $K_D$ values for the individual antibody/LLT1 complexes.

Similarly, the specificity of an interaction may be assessed by determining and comparing the $K_D$ value for the interaction of interest, e.g. a specific interaction between an anti-LLT1 antibody and LLT1, with the $K_D$ value of an interaction that is not of interest.

Typically, the $K_D$ for the antibody with respect to the target (LLT1) will be 2-fold, preferably 5-fold, more preferably 10-fold less than its $K_D$ with respect to other, non-target molecules, such as unrelated material or accompanying material in the environment. More preferably, the $K_D$ will be 50-fold less, such as 100-fold less, or 200-fold less; even more preferably 500-fold less, such as 1,000-fold less, or 10,000-fold less. An antibody of the invention may have a $K_D$ for its target of $1 \times 10^{-7}$ M or less, $1 \times 10^{-8}$ M or less, or $1 \times 10^{-9}$ M or less, or $1 \times 10^{-10}$ M or less, $1 \times 10^{-11}$ M or less, or $1 \times 10^{-12}$ M or less. The $K_D$ for the antibody with respect to LLT1 may be at least 2-fold, such as at least 3-fold, such as at least 4-fold, such as at least 5-fold, such as at least 10-fold less than the $K_D$ of said mAB with another lectin of the C-type lectin superfamily, such as CLEC2A, AICL or CD69.

The value of this dissociation constant can be determined directly by well-known methods, and can be computed even for complex mixtures by methods such as those set forth in Caceci et al. (Byte 9:340-362, 1984). For example, the $K_D$ may be established using a double-filter nitrocellulose filter binding assay, such as that disclosed by Wong & Lohman (Proc. Natl. Acad. Sci. USA 90, 5428-5432, 1993). Binding of an antibody to LLT1 can also be evaluated using protocols based on ELISA, Western blotting, BIACORE, inter alia, as described, for example, in Coligan et al., eds Current Protocols in Immunology, Greene Publishing Assoc. and Wiley Interscience, N.Y. (1992, 1993). Several suitable binding assays are described in greater detail in the examples.

For example, the ability of an antibody to bind to LLT1 can be tested in a standard flow cytometry assay using e.g. HEK293 cells transfected with an expression vector carrying cDNA encoding LLT1. Hybridoma cell culture supernatant or purified antibody is incubated with HEK293 cells transfected (or not) with LLT1 cDNA. After incubation, cells are washed with DMEM/2% FCS, and incubated with APC-conjugated donkey anti-mouse secondary Ab-fragments. After extensive washing with PBS, Ab-binding to living cells is analyzed using flow cytometry. This assay identifies antibodies that bind to LLT1 that is expressed on the cell surface.

In another typical binding assay, the ability of an antibody to bind to LLT1 can be tested in a standard Enzyme-Linked Immunosorbent Assay (ELISA) using e.g. LLT1-human Fc fusion protein. Nunc immunoplates are coated with LLT1-hFc protein. After blocking with 0.05% Tween-20 in PBS, culture supernatants from the hybridoma cells or purified antibody are added and the plates are incubated overnight. Horse-radish peroxidase (HRPO)-labelled goat anti-mouse Ab's are added followed by another hour of incubation. Antibody binding are developed with TMB-substrate and absorbance at 450 nm are measured on an ELISA-reader. This assay identifies antibodies that bind to recombinant LLT1-hFc fusion protein.

In yet another typical binding assay, the ability of an antibody to bind to LLT1 can be tested in a standard Western blotting (WB) assay using e.g. protein extract from cells transfected with LLT1 cDNA. Protein is extracted from parental C1R cells and C1R-LLT1 transfectants and separated by SDS-polyacrylamide gel electophoresis under reducing or non-reducing conditions. A molecular weight marker is run in parallel in the same gel. The separated proteins are blotted onto filter and stained with anti-LLT12F1 antibody according to standard procedure. This assay identifies antibodies that bind to denatured LLT1 protein.

In a fourth typical binding assay, the kinetic parameters for the interaction of anti-LLT1 antibodies with LLT1 can be evaluated by BIACORE analysis. Surface plasmon resonance measurements are performed on a BIACORE T100 apparatus. LLT1-Fc fusion protein is immobilized covalently to carboxyl groups in the dextran layer on a Sensor Chip CM5. Following activation of the sensor chip surface, antibodies diluted in coupling buffer are injected. Deactivation of the remaining activated groups is performed using 100 mM ethanolamine pH 8. This assay determines the kinetic parameters (e.g. KD) for binding of anti-LLT1 antibodies to LLT1 protein.

The ability of an anti-LLT1 antibody to block the interaction between LLT1 and its receptor, CD161, can be evaluated in a typical binding assay using e.g. multimeric complexes of an LLT1-Fc fusion protein. A multimeric complex is generated by incubating the LLT1-Fc fusion protein with protein A-biotin at a molar ratio of 1:1. Saturating amounts of purified hIgG are added to block the remaining free protein A sites. The complex is conjugated to streptavidin-allophycocyanin and incubated with 293T-CD161 cells in the presence or absence of anti-LLT1 antibody. Binding of LLT1-multimers to 293T-CD161 cells is evaluated by flow cytometry. This assay determines the ability of anti-LLT1 antibodies to block the binding of LLT1-multimers to cell surface-expressed CD161.

A competitive binding assay can be conducted in which the binding of the antibody to its target (LLT1) is compared to binding of the target by another ligand of that target, such as another antibody. The concentration at which 50% inhibition occurs is known as the Ki. Under ideal conditions, the Ki is equivalent to $K_D$. The Ki value will never be less than the $K_D$, so measurement of Ki can conveniently be substituted to provide an upper limit for $K_D$.

An antibody that specifically binds LLT1 may bind LLT1 with a high affinity (that is, exhibiting a low $K_D$ as discussed above) and may bind other, non-target molecules with a lower affinity. For example, the antibody may bind to non-target molecules with a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more. An antibody of the invention is preferably capable of binding to its target with an affinity that is at least two-fold, 10-fold, 50-fold, 100-fold 200-fold, 500-fold, 1,000-fold or 10,000-fold, greater than its affinity for another, non-target molecule. An antibody of the invention may be capable of binding LLT1 with a higher affinity than other, known anti-LLT1 antibodies, such as "MAB3480" (R&D Systems), "4C7" (Abnova), "L9.7" (U.S. Pat. No. 6,455,683, U.S. Pat. No. 7,524,622) and "402624" (Rosen et al. (2008).

The term "complementarity-determining region" ("CDR") or "hypervariable region", when used herein, refers to the amino acid residues of an antibody that are responsible for antigen binding. The CDRs are generally comprised of amino acid residues 24-34 (L1), 50-56 (L2) and 89-97 (L3) in the light-chain variable domain and 31-35 (H1), 50-65 (H2) and 95-102 (H3) in the heavy-chain variable domain; (Kabat et al. (1991) Sequences of Proteins of Immunological Interest, Fifth Edition, U.S. Department of Health and Human Services, NIH Publication No. 91-3242) and/or those residues from a "hypervariable loop" (residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol. 1987; 196:901-917). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "framework region" or "FR" residues refer to those VH or VL amino acid residues that are not within the CDRs, as defined herein.

An antibody of the invention may comprise a CDR region from the specific antibodies disclosed herein, such as a CDR region from within SEQ ID NOs: 4, 7, 10 and/or 13. Such an antibody will, preferably, retain the ability to specifically bind to LLT1. As shown in FIGS. 1 and 2 and using the Kabat definition, the CDR sequences within the light chain of an antibody of the invention may be identified at amino acids 24 to 40, 56 to 62 and 94 to 102 of SEQ ID NOs: 7 or 13. The CDR sequences within the heavy chain of an antibody of the invention may be identified at amino acids 31 to 35, 50 to 66 and 99 to 108 of SEQ ID NO: 4 or at amino acids 31 to 35, 50 to 66 and 98 to 109 of SEQ ID NO: 10.

An antibody of the invention may have a heavy chain that comprises:
- a CDR1 sequence of amino acids 31 to 35 (SYGMS) of SEQ ID NO:4, wherein one of these amino acids may be substituted by a different amino acid; and/or
- a CDR2 sequence of amino acids 50 to 66 (TINSNGGRT-FYPDSVKG) of SEQ ID NO:4, wherein one, two or three of these amino acids may be substituted by a different amino acid; and/or
- a CDR3 sequence of amino acids 99 to 108 (DGGYWAH-FDY) of SEQ ID NO:4, wherein one, two or three of these amino acids may be substituted by a different amino acid.

An antibody of the invention may have a light chain that comprises:
- a CDR1 sequence of amino acids 24 to 40 (RSSQSIVH-SNGNTYLE) of SEQ ID NO: 7, wherein one, two or three of these amino acids may be substituted with a different amino acid; and/or
- a CDR2 sequence of amino acids 56 to 62 (KVSNRFS) of SEQ ID NO: 7, wherein one or two of these amino acids may be substituted with a different amino acid; and/or
- a CDR3 sequence of amino acids 94 to 102 (FQGSH-VPWT) of SEQ ID NO: 7, wherein one or two of these amino acids may be substituted with a different amino acid.

An antibody of the invention may comprise any combination of the above CDR regions.

An antibody of the invention may comprise:
- a CDR1 sequence of amino acids 31 to 35 (SYGMS) of SEQ ID NO:4, wherein one of these amino acids may be substituted by a different amino acid; and
- a CDR2 sequence of amino acids 50 to 66 (TINSNGGRT-FYPDSVKG) of SEQ ID NO:4, wherein one, two or three of these amino acids may be substituted by a different amino acid; and
- a CDR3 sequence of amino acids 99 to 108 (DGGYWAH-FDY) of SEQ ID NO:4, wherein one, two or three of these amino acids may be substituted by a different amino acid.

and wherein the light chain of said antibody comprises:
- a CDR1 sequence of amino acids 24 to 40 (RSSQSIVH-SNGNTYLE) of SEQ ID NO: 7, wherein one, two or three of these amino acids may be substituted with a different amino acid; and
- a CDR2 sequence of amino acids 56 to 62 (KVSNRFS) of SEQ ID NO: 7, wherein one or two of these amino acids may be substituted with a different amino acid; and
- a CDR3 sequence of amino acids 94 to 102 (FQGSH-VPWT) of SEQ ID NO: 7, wherein one or two of these amino acids may be substituted with a different amino acid.

A monoclonal antibody according to any one of embodiments 1-3, wherein the light chain of said antibody comprises SEQ ID NO: 7 and the heavy chain of said antibody comprises SEQ ID NO: 4.

An antibody of the invention may have a heavy chain that comprises:
- a CDR1 sequence of amino acids 31 to 35 (DYYMH) of SEQ ID NO:10, wherein one of these amino acids may be substituted by a different amino acid; and/or
- a CDR2 sequence of amino acids 50 to 66 (WID-PENGDTEYAPKFQG) of SEQ ID NO:10, wherein one, two or three of these amino acids may be substituted by a different amino acid; and/or
- a CDR3 sequence of amino acids 98 to 109 (EIITTTAW-FTY) of SEQ ID NO:10, wherein one, two or three of these amino acids may be substituted by a different amino acid.

An antibody of the invention may have a light chain that comprises:
- a CDR1 sequence of amino acids 24 to 40 (KSSQSLLYT-NGKTYLNW) of SEQ ID NO: 13, wherein one, two or three of these amino acids may be substituted with a different amino acid; and/or a CDR2 sequence of amino acids 56 to 62 (VSKLDSG) of SEQ ID NO: 13, wherein one or two of these amino acids may be substituted with a different amino acid; and/or a CDR3 sequence of amino acids 94 to 102 (LQNTHF-PHT) of SEQ ID NO: 13, wherein one or two of these amino acids may be substituted with a different amino acid.

An antibody of the invention may comprise:

a CDR1 sequence of amino acids 31 to 35 (DYYMH) of SEQ ID NO:10, wherein one of these amino acids may be substituted by a different amino acid; and a CDR2 sequence of amino acids 50 to 66 (WID-PENGDTEYAPKFQG) of SEQ ID NO:10, wherein one, two or three of these amino acids may be substituted by a different amino acid; and a CDR3 sequence of amino acids 98 to 109 (EIITTTAW-FTY) of SEQ ID NO:10, wherein one, two or three of these amino acids may be substituted by a different amino acid;

and wherein the light chain of said antibody comprises:

a CDR1 sequence of amino acids 24 to 40 (KSSQSLLYT-NGKTYLNW) of SEQ ID NO: 13, wherein one, two or three of these amino acids may be substituted with a different amino acid; and a CDR2 sequence of amino acids 56 to 62 (VSKLDSG) of SEQ ID NO: 13, wherein one or two of these amino acids may be substituted with a different amino acid; and a CDR3 sequence of amino acids 94 to 102 (LQNTHF-PHT) of SEQ ID NO: 13, wherein one or two of these amino acids may be substituted with a different amino acid.

Substitution preferably occurs in the framework regions of the sequences.

A monoclonal antibody of the invention may have a light chain that comprises SEQ ID NO: 7. A monoclonal antibody of the invention may have a light chain that comprises SEQ ID NO: 13. A monoclonal antibody of the invention may have a heavy chain that comprises SEQ ID NO: 4. A monoclonal antibody of the invention may have a heavy chain that comprises SEQ ID NO: 10.

The term "identity", as known in the art, refers to a relationship between the sequences of two or more polypeptides, as determined by comparing the sequences. In the art, "identity" also means the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3.times. the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., Proc. Natl. Acad. Sci. USA 89, 10915-10919 (1992) for the BLOSUM 62 comparison matrix) is also used by the algorithm.

Preferred parameters for a peptide sequence comparison include the following:

Algorithm: Needleman et al., J. Mol. Biol. 48, 443-453 (1970); Comparison matrix: BLOSUM 62 from Henikoff et al., PNAS USA 89, 10915-10919 (1992); Gap Penalty: 12, Gap Length Penalty: 4, Threshold of Similarity: 0.

The GAP program is useful with the above parameters. The aforementioned parameters are the default parameters for peptide comparisons (along with no penalty for end gaps) using the GAP algorithm.

The present invention thus provides antibodies having specific VH and VL amino acid sequences and variants and fragments thereof which maintain the function or activity of these VH and VL domains.

The term "epitope", as used herein, is defined in the context of a molecular interaction between an "antigen binding polypeptide" (Ab) and its corresponding "antigen" (Ag). Generally, the term "epitope" refers to the area or region on an Ag to which an Ab specifically binds, i.e. it is the area or region in physical contact with the Ab. A protein epitope may comprise amino acid residues in the Ag that are directly involved in binding to a Ab (also called the immunodominant component of the epitope) and other amino acid residues, which are not directly involved in the binding, such as amino acid residues of the Ag which are effectively blocked by the Ab (in other words, the amino acid residue is within the "solvent-excluded surface" and/or the "footprint" of the Ab). The term epitope herein includes both types of binding sites of any particular region of LLT1 that specifically binds to an anti-LLT1 antibody, or another LLT1-specific agent according to the invention, unless otherwise stated (e.g., in some contexts the invention relates to antibodies that bind directly to particular amino acid residues). LLT1 may comprise a number of different epitopes, which may include, without limitation, (1) linear peptide antigenic determinants, (2) conformational antigenic determinants which consist of one or more non-contiguous amino acids located near each other in the mature LLT1 conformation; and (3) post-translational antigenic determinants which consist, either in whole or part, of molecular structures covalently attached to LLT1, such as carbohydrate groups.

The epitope for a given antibody (Ab)/antigen (Ag) pair can be defined and characterized at different levels of detail using a variety of experimental and computational epitope mapping methods. The experimental methods include mutagenesis, X-ray crystallography, Nuclear Magnetic Resonance (NMR) spectroscopy, Hydrogen deuterium eXchange Mass Spectrometry (HX-MS) and various competition binding methods. As each method relies on a unique principle, the description of an epitope is intimately linked to the method by which it has been determined. Thus, the epitope for a given Ab/Ag pair will be defined differently, depending on the epitope mapping method employed.

At its most detailed level, the epitope for the interaction between the Ag and the Ab can be defined by the spatial coordinates defining the atomic contacts present in the Ag-Ab interaction, as well as information about their relative contributions to the binding thermodynamics. At a less detailed level, the epitope can be characterized by the spatial coordinates defining the atomic contacts between the Ag and Ab. At a further, less detailed, level the epitope can be characterized by the amino acid residues that it comprises as defined by a specific criterium, e.g. distance between atoms in the Ab and the Ag. At a further less detailed level the epitope can be characterized through function, e.g. by competition binding with other Abs. The epitope can also be defined more generically as comprising amino acid residues for which substitution by another amino acid will alter the characteristics of the interaction between the Ab and the Ag.

In the context of an X-ray derived crystal structure, defined by spatial coordinates of a complex between an Ab, e.g. a Fab fragment, and its Ag, the term epitope is herein, unless otherwise specified or contradicted by context, specifically defined as LLT1 residues characterized by having a heavy atom (i.e. a non-hydrogen atom) within a distance of 4 Å from a heavy atom in the Ab.

From the fact that descriptions and definitions of epitopes, dependant on the epitope mapping method used, are obtained at different levels of detail, it follows that comparison of epitopes for different Abs on the same Ag can similarly be conducted at different levels of detail.

Epitopes described on the amino acid level, e.g. determined from an X-ray structure, are said to be identical if they contain the same set of amino acid residues. Epitopes are said to overlap if at least one amino acid is shared by the epitopes. Epitopes are said to be separate (unique) if no amino acid residue are shared by the epitopes.

Epitopes characterized by competition binding are said to be overlapping if the binding of the corresponding Ab's are mutually exclusive, i.e. binding of one Ab excludes simultaneous binding of the other Ab. The epitopes are said to be separate (unique) if the Ag is able to accommodate binding of both corresponding Ab's simultaneously.

The definition of the term "paratope" is derived from the above definition of "epitope" by reversing the perspective. Thus, the term "paratope" refers to the area or region on the Ab to which an Ag specifically binds, i.e. to which it makes physical contact to the Ag.

In the context of an X-ray derived crystal structure defined by spatial coordinates of a complex between an Ab, e.g. a Fab fragment, and its Ag, the term paratope is herein, unless otherwise specified or contradicted by context, specifically defined as Ag residues characterized by having a heavy atom (i.e. a non-hydrogen atom) within a distance of 4 Å from a heavy atom in LLT1.

The epitope and paratope for a given antibody (Ab)/antigen (Ag) pair may be identified by routine methods. For example, the general location of an epitope may be determined by assessing the ability of an antibody to bind to different fragments or variant LLT1 polypeptides. The specific amino acids within LLT1 that make contact with an antibody (epitope) and the specific amino acids in an antibody that make contact with LLT1 (paratope) may also be determined using routine methods. For example, the antibody and target molecule may be combined and the Ab/Ag complex may be crystallised. The crystal structure of the complex may be determined and used to identify specific sites of interaction between the antibody and its target.

"Epitope binning" refers to the use of competitive binding assays to identify pairs of antibodies that are, or are not, capable of binding an antigen such as LLT1 simultaneously, thereby identifying antibodies that bind to the same, or overlapping epitopes of LLT1. Families of antibodies (or bins) that have the same, or overlapping, binding specificity can then be used to help define specific epitopes on LLT1. Epitope binning experiments provide evidence that antigenically distinct epitopes are present. However, by themselves, they do not identify, or "map" the epitope to a specific amino acid sequence or location on LLT1. Competition for binding can be evaluated for any pair of antibodies or fragments.

In addition to the competitive binding of antibodies, epitope binning can also be used to identify antibodies to either a receptor or a ligand that competitively interfere or the ligand mediated activation of its receptor. Frequently, favourable properties of a family (or bin) of antibodies can be correlated with a binding to a specific epitope defined by the antibody bin.

Once a suitable antibody has been identified and selected, the amino acid sequence of the antibody may be identified by methods known in the art. The genes encoding the antibody can be cloned using specific and/or degenerate primers. The antibody may be recombinantly produced by routine methods.

The function of any antibody may be tested using a variety of well known assays, such as cytotoxicity assays and cytokine production assays, in order to determine whether or not it may be an antibody according to the current invention.

If an antibody reduces or blocks LLT1 interactions with CD161, it may increase the cytotoxicity of CD161-restricted lymphocytes. This can be evaluated using a typical cytotoxicity assay. For example, the ability of an antibody to reduce CD161-mediated signaling can be tested in a standard 4-hour in vitro cytotoxicity assay using, for example, NK cells that express CD161 and target cells that express LLT1. Said NK cells do not efficiently kill targets that express LLT1 because CD161 recognizes LLT1 leading to initiation and propagation of inhibitory signaling that prevents lymphocyte-mediated cytolysis. The in vitro cytotoxicity assay is described in Coligan et al., eds *Current Protocols in Immunology*, Greene Publishing Assoc. and Wiley Interscience, N.Y. (1992, 1993). The target cells are labeled with 51Cr prior to addition of NK cells, and then the killing is estimated as proportional to the release of 51Cr from the cells to the medium, as a result of killing.

In one embodiment, antibodies of the invention are capable of stimulating the cytotoxicity of NK cells by at least 10%, such as at least 20%, such as at least 30%, such as at least 40%, such as at least 50%, such as at least 60%, such as at least 70%, such as at least 80%, such as at least 90%, such as at least 100%, as may be measured in the standard 4-hour in vitro cytotoxicity assay.

In another standard in vitro cytotoxicity assay, CD107a expression on the NK cells is measured, as CD107a surface expression correlates with NK cell-mediated lysis of target cells (Alter et al 2004 Journal of Immunological Methods 294:15-22) The addition of an antibody that prevents LLT1 from binding to CD161 results in prevention of the initiation and propagation of inhibitory signalling via CD161. Therefore, addition of such agents results in increases in lymphocyte-mediated killing of the target cells. This step thereby identifies agents that prevent LLT1-mediated negative signaling by, e.g. blocking LLT1 binding to CD161. In a particular CD107a cytotoxicity assay, CD161-expressing NK effector-cells can kill LLT1-negative C1R cells, but less well LLT1-expressing C1R-LLT1 cells. Thus, NK effector cells kill less efficiently LLT1+ C1R cells due to LLT1-induced inhibitory signaling. When NK cells are pre-incubated with blocking anti-LLT1 antibodies according to the present invention in such a CD107a cytotoxicity assay, LLT1-expressing C1R cells are more efficiently killed. In another particular Cd107a cytotoxicity assay, pre-incubation of the NK cells with blocking anti-LLT1 antibodies results in more efficiently killing of Raji cells.

The inhibitory or potentiating activity of an antibody of this invention can also be assessed in any of a number of other ways, e.g. by its effect on intracellular free calcium as described, e.g. in Soviri et. al., J. Exp. Med. 1997; 186:1129-1136, the disclosure of which is herein incorporated by reference.

In particular embodiments of the invention, an antibody is capable of stimulating the cytotoxicity of NK cells by at least 10%, such as at least 20%, such as at least 30%, such as at least 40%, such as at least 50%, such as at least 60%, such as at least 70%, such as at least 80%, such as at least 90%, such as at least 100%, as may be measured in a CD107a cytotoxicity assay.

The activity of a cytotoxic lymphocyte can also be addressed using a cytokine-production assay, wherein NK cells are incubated with target cells to induce the cytokine production of the NK cells (for example IFN-γ and TNF-α production). Such a cytokine-production assay is carried out by standard methods that are well known in the art, as described, for example, by Coligan et al, eds *Current Protocols in Immunology*, Greene Publishing Assoc. and Wiley Interscience, N.Y. In a particular IFN-γ production assay, co-culture of NK cells with C1R cells induces IFN-γ production by NK cells. LLT1+ C1R cells induces IFN-γ production by NK cells less efficiently. When NK cells are pre-incubated with blocking anti-LLT1 antibodies according to the present invention, in such an IFN-γ production assay, LLT1-expressing C1R cells induce IFN-γ production by NK cells more efficiently. In another particular cytokine-production assay pre-incubation of the NK cells with blocking anti-LLT1 antibodies increases IFN-γ production by the NK cells when co-cultured with Raji cells.

In one embodiment, an antibody preparation causes at least 10% augmentation in the cytokine-production assay of a CD161-restricted lymphocyte, preferably at least a 40% or 50% augmentation in NK cytokine production, or more preferably at least a 70% augmentation in NK cytokine production.

In one embodiment, a monoclonal antibody of the invention is capable of stimulating the cytokine production of NK cells by at least 50%, such as at least 100%, such as at least 200%, such as at least 300%, such as at least 400%, such as at least 500%, as may be measured in a cytokine production assay.

In another embodiment, a monoclonal antibody of the invention is capable of reducing the interferon-gamma (INF-γ) production of CD161-expressing cells by at least 10%, such as at least 20%, such as at least 30%, such as at least 40%, such as at least 50%, such as at least 60%, such as at least 70%, such as at least 80%, such as at least 90%, such as 100%, as may be measured in a cytokine production assay.

The ability of an anti-LLT1 antibody to induce antibody-dependent cell-mediated cytotoxicity (ADCC) can be evaluated in several, well known assays. Protocols based on $^{51}$Cr-release and CD107a flow cytometry are suitable for use and are well known in the art, as described for example in Coligan et al., eds Current Protocols in Immunology, Greene Publishing Assoc. and Wiley Interscience, N.Y. (1992, 1993). Effector cells with receptors for the Fc portion of immunoglobulin produce target cell lysis by attachment to the Fc portion of antibodies that are bound to target cells via their antigen-combining sites. For example, effector cells with receptors for the Fc portion of an anti-LLT1 antibody produce lysis of LLT1-expressing cells.

The invention also relates to polynucleotides that encode antibodies of the invention. Thus, a polynucleotide of the invention may encode any antibody as described herein. The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

In one embodiment, a polynucleotide of the invention comprises a sequence which encodes a VH or VL amino acid sequence as described above. For example, a polynucleotide of the invention may encode a polypeptide comprising the sequence of SEQ ID NO: 4 and/or SEQ ID NO: 7 and/or SEQ ID NO: 10 and/or SEQ ID NO: 13, or variants or fragments thereof, as described above. Such polynucleotides may consist of or comprise a nucleic acid sequence of any one or a combination of SEQ ID NOs: 2, 3, 5, 6, 8, 9, 11 or 12. Suitable polynucleotide sequences may, alternatively, be variants of one or more of these specific polynucleotide sequences. For example, a variant may be a substitution, deletion or addition variant of any of the above nucleic acid sequences. A variant polynucleotide may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to a polynucleotide of any one of SEQ ID NOs: 2, 3, 5, 6, 8, 9, 11 or 12, such as at least 80%, such as at least 85%, such as at least 90%, or at least 95%, such as at least 96%, such as at least 97%, such as at least 98% or such as at least 99% homologous thereto. Homology may exist over a region of at least 15, preferably at least 30, for instance at least 40, 50, 60, 70, 80, 90, 100, 200 or more contiguous nucleotides.

A homologue may differ from a sequence in the relevant polynucleotide by less than 3, 5, 10, 15, 20 or more mutations (each of which may be a substitution, deletion or insertion). These mutations may be measured over a region of at least 30, for instance at least 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

Polynucleotide "fragments" according to the invention may be made by truncation, e.g. by removal of one or more nucleotides from one or both ends of a polynucleotide. Up to 10, up to 20, up to 30, up to 40, up to 50, up to 75, up to 100, up to 200 or more amino acids may be removed from the 3' and/or 5' end of the polynucleotide in this way. Fragments may also be generated by one or more internal deletions. Such fragments may be derived from a sequence of SEQ ID NOs: 2, 3, 5, 6, 8, 9, 11 or 12 or may be derived from a variant polynucleotide as described herein.

An antibody of the invention may thus be produced from or delivered in the form of a polynucleotide which encodes, and is capable of expressing, it. Where the antibody comprises two or more chains, a polynucleotide of the invention may encode one or more antibody chains. For example, a polynucleotide of the invention may encode an antibody light chain, an antibody heavy chain or both. Two polynucleotides may be provided, one of which encodes an antibody light chain and the other of which encodes the corresponding antibody heavy chain. Such a polynucleotide or pair of polynucleotides may be expressed together such that an antibody of the invention is generated.

Polynucleotides of the invention can be synthesised according to methods well known in the art, as described by way of example in Sambrook et al (1989, Molecular Cloning—a laboratory manual; Cold Spring Harbor Press).

The nucleic acid molecules of the present invention may be provided in the form of an expression cassette which includes control sequences, signal peptide sequences operably linked to the inserted sequence, thus allowing for expression of the antibody of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers, signal peptide sequences and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes cells that have been modified to express an antibody of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors or expression cassettes encoding for an antibody of the invention include mammalian HEK293, CHO, BHK, NSO and human retina cells. Preferably the cell line selected will be one which is not only stable, but also allows for mature glycosylation and cell surface expression of a polypeptide.

Such cell lines of the invention may be cultured using routine methods to produce an antibody of the invention, or may be used therapeutically or prophylactically to deliver antibodies of the invention to a subject. Alternatively, polynucleotides, expression cassettes or vectors of the invention may be administered to a cell from a subject ex vivo and the cell then returned to the body of the subject.

In another aspect, the present invention provides compositions and formulations comprising molecules of the invention, such as the antibodies, polynucleotides, vectors and cells described herein. For example, the invention provides a pharmaceutical composition that comprises one or more antibodies of the invention, formulated together with a pharmaceutically acceptable carrier.

Accordingly, one object of the invention is to provide a pharmaceutical formulation comprising such an antibody which is present in a concentration from 1 mg/ml to 500 mg/ml, and wherein said formulation has a pH from 2.0 to 10.0. The formulation may further comprise a buffer system, preservative(s), tonicity agent(s), chelating agent(s), stabilizers and surfactants. The use of preservatives, isotonic agents, chelating agents, stabilizers and surfactants in pharmaceutical compositions is well-known to the skilled person. Reference may be made to Remington: *The Science and Practice of Pharmacy*, 19$^{th}$ edition, 1995.

In one embodiment, the pharmaceutical formulation is an aqueous formulation. Such a formulation is typically a solution or a suspension. The terms "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, to which the physician or the patient adds solvents and/or diluents prior to use.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

Antibodies of the invention may be co-administered with one or other more other therapeutic agents or formulations. The other agent may be an agent that enhances the effects of the antibody of the invention. The other agent may be intended to treat other symptoms or conditions of the patient. For example, the other agent may be an analgesic, an anaesthetic, an immunosuppressant or an anti-inflammatory agent. The other agent may be another monoclonal antibody, such as one of those described in international patent applications, WO06/070286, WO08/009,545 and WO09/077,483.

Combined administration of two or more agents may be achieved in a number of different ways. In one embodiment, the antibody and the other agent may be administered together in a single composition. In another embodiment, the antibody and the other agent may be administered in separate compositions as part of a combined therapy. For example, the modulator may be administered before, after or concurrently with the other agent.

The antibodies, other molecules and compositions of the present invention have numerous in vitro and in vivo therapeutic uses involving the treatment and prevention of cancer or autoimmune disorders. The antibody of the current invention may be used to treat diseases that are characterised by abnormal LLT-1 expression. For example, the antibody may be utilised to remove LLT-1 expressing cancer cells in a cancer patient. The antibody according to the current invention may also find utility in the treatment of autoimmune diseases such as autoimmune haemolytic anaemia, Goodpasture's syndrome, acute febris rheumatica, insulin-resistant diabetes mellitus, systemic lupus erythematosus (SLE), rheumatoid arthritis (RA), multiple sclerosis (MS), Type I diabetes, myasthenia gravis, chronic active hepatitis, primary biliary cirrhosis, pre-eclampsia, rheumatoid arthritis, Guillain-Barrés syndrome, pernicious anaemia, systemic vasculitis, Wegeners granulomatosis, Sjögren's syndrome, sclerodermia, Hashimoto's thyroiditis, vitiligo and coeliac disease.

An antibody according to the current invention may bind LLT1 such that the immune system is modulated. As explained above, antibodies of the invention may modify the activity of LLT1-bearing cells or CD161-bearing cells. Antibodies identified as having the required binding properties may thus be further tested to determine their biological activity, as illustrated in the examples. Thus, methods may be used to identify suitable antibodies that are capable of binding to LLT1 and that are thus capable of initiating a desirable biological response.

An antibody of the invention may bind to LLT1 and in doing so may "block" or inhibit binding of LLT1 to its receptor, CD161. An antibody according to the current invention may bind LLT1 such that any one of the effects mediated by LLT1 is modified. The antibody of the current invention may bind LLT1 such that any one of the CD161-mediated effects of LLT1 is modified. Hence, an antibody according to the current invention may block LLT1 which is expressed on the surface of activated monocytes and lymphocytes, such as activated B-cells, activated dendritic cells (DCs), activated NK cells and activated T-cells. An antibody of the current invention may prevent, or reduce, co-receptor stimulation between LLT1-bearing monocytes and lymphocytes, such as B-cells and dendritic cells, and CD161-bearing T-cells and/or NK cells. An antibody according to the current invention may enhance NK cell cytokine production, such as INF-γ production. An antibody according to the current invention may enhance NK cell cytotoxicity. An antibody according to the current invention may result in the depletion of LLT1-expressing malignant (cancer) cells. Such depletion may occur by means of antibody-dependent cellular cytotoxicity (ADCC) or complement-dependent cytotoxicity (CDC). LLT1-expressing malignant cells may be such as malignant B-cell lymphoma cells. Other LLT1-expressing cells may be in chronically inflamed tissue, such as in the inflamed synovial tissue of individuals with rheumatoid arthritis (RA), such as in the inflamed mucous and sub-mucosal tissue of the GI tract of individuals with inflammatory bowel diseases (Crohn's disease and ulcerative colitis).

The term "treatment", as used herein, refers to the medical therapy of any human or other animal subject in need thereof. Said subject is expected to have undergone physical examination by a medical practitioner or a veterinary medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Thus, said treatment may be prophylactic, palliative, symptomatic and/or curative. In terms of the present invention, prophylactic, palliative, symptomatic and/or curative treatments may represent separate aspects of the invention.

Thus, an antibody of the invention may be administered parenterally. An antibody of the invention may be administered intravenously. An antibody of the invention may be administered intramuscularly. An antibody of the invention may be administered subcutaneously. Alternatively, an antibody of the invention may be administered perorally or topically. An antibody of the invention may be administered prophylactically. An antibody of the invention may be administered therapeutically (on demand).

In therapeutic applications, antibodies or compositions are administered to a subject already suffering from a disorder or condition as described above, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as "therapeutically effective amount". For example, where the treatment alleviates the pain of rheumatoid arthritis, therapy may be defined as a decrease in the amount of pain that a patient experiences.

In prophylactic or preventative applications, antibodies or compositions are administered to a subject at risk of a disorder or condition as described above, in an amount sufficient to prevent or reduce the subsequent effects of the condition or one or more of its symptoms. An amount adequate to accomplish this is defined as a "prophylactically effective amount". For example, where the treatment is to prevent unwanted bleeding, a prophylactic effect may be defined as the prevention of bleeding or a reduced period or quantity of bleeding compared to that that would be seen in the absence of the modulator.

Effective amounts for each purpose will depend on the severity of the disease or injury as well as the weight and general state of the subject.

As used herein, the term "subject" includes any human or non-human animal. The term "non-human animal" includes all vertebrates, e.g., mammals and non-mammals, such as non-human primates, sheep, dogs, cats, horses, cows, chickens, amphibians, reptiles, and so forth. Unless contradicted by context, the words "subject", "individual" and "patient" are herein used synonymously.

A suitable dosage of an antibody of the invention may be determined by a skilled medical practitioner. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular antibody employed, the route of administration, the time of administration, the rate of excretion of the antibody, the duration of the treatment, other drugs, compounds and/or materials used in combination with the particular compositions employed, the age, sex, weight, condition, general health and prior medical history of the patient being treated, and like factors well known in the medical arts.

A suitable dose of an antibody of the invention may be, for example, in the range of from about 0.1 µg/kg to about 100 mg/kg body weight of the patient to be treated. For example, a suitable dosage may be from about 1 µg/kg to about 10 mg/kg body weight per day or from about 1 mg/kg to about 5 mg/kg body weight per day. A suitable dose of an antibody of the invention may be in the range of from 2 to 200 mg/kg, such as about 150-200 mg/kg, such as about 150-170 mg/kg, such as about 100-150 mg/kg, such as about 50-100 mg/kg, such as about 70-90 mg/kg, such as about 10-50 mg/kg, such as about 10-30 mg/kg.

Other suitable dosages may be approximately 0.1-10 mg/kg, such as approximately 0.1-1 mg/kg, such as approximately 1-2 mg/kg or approximately 2-3 mg/kg or approximately 4-5 mg/kg or approximately 5-6 mg/kg or approximately 6-7 mg/kg or approximately 7-8 mg/kg or approximately 8-9 mg/kg or approximately 9-10 mg/kg; or approximately 10-21 mg/kg, such as approximately 10-11 mg/kg, or approximately 11-12 mg/kg, or approximately 12-13 mg/kg, or approximately 13-14 mg/kg, or approximately 14-15 mg/kg, or approximately 15-16 mg/kg, or approximately 16-17 mg/kg, or approximately 17-18 mg/kg, or approximately 18-19 mg/kg, or approximately 19-20 mg/kg or approximately 20-21 mg/kg.

The amount of monoclonal antibody administered to a subject may be such that its administration results in a subject plasma concentration of about 10 µg/ml to about 40 µg/ml, such as about 15-35 µg/ml, such as about 10-15 µg/ml, such as about 15-20 µg/ml, such as about 20-25 µg/ml, such as about 25-30 µg/ml, such as about 30-35 µg/ml, such as about 35-40 µg/ml, of said monoclonal antibody. Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Antibodies may be administered in a single dose or in multiple doses. The multiple doses may be administered via the same or different routes and to the same or different locations. Alternatively, antibodies can be administered as a sustained release formulation, in which case less frequent administration is required. Dosage and frequency may vary depending on the half-life of the antibody in the patient and the duration of treatment that is desired. The dosage and frequency of administration can also vary depending on whether the treatment is prophylactic or therapeutic. In prophylactic applications, a relatively low dosage may be administered at relatively infrequent intervals over a long period of time. In therapeutic applications, a relatively high dosage may be administered, for example until the patient shows partial or complete amelioration of symptoms of disease.

Embodiments

The following is a non-limiting list of embodiments of the present invention:

Embodiment 1: A monoclonal antibody that is capable of specifically binding to LLT1 and that blocks the interaction between LLT1 and CD161.

Embodiment 2: The monoclonal antibody according to embodiment 1, which is capable of removing LLT1-expressing cells by means of antibody-dependent cell-mediated cytotoxicity (ADCC), as may be measured in the ADCC assay.

Embodiment 3: The monoclonal antibody according to any one of embodiments 1-2, which is capable of removing LLT1-expressing cells by means of complement-dependent cytotoxicity (CDC), as may be measured in the CDC assay.

Embodiment 4: The monoclonal antibody according to any one of embodiments 1-3, which is capable of stimulating the cytokine production and/or the cytotoxicity of NK cells.

Embodiment 5: The monoclonal antibody according to embodiment 4, which is capable of stimulating the cytotoxicity of NK cells by at least 1%, such as at least 2%, such as at least 3%, such as at least 4%, such as at least 5%, such as at least 6%, such as at least 7%, such as at least 8%, such as at least 9%, such as at least 10%, such as at least 20%, such as at least 30%, such as at least 40%, such as at least 50%, such as at least 60%, such as at least 70%, such as at least 80%, such as at least 90%, such as at least 100%, as may be measured in a cytotoxicity assay, such as the 4-hour in vitro cytotoxicity assay or the CD107a cytotoxicity assay.

Embodiment 6: The monoclonal antibody according to any one of embodiments 4-5, which is capable of stimulating the cytokine production of NK cells by at least 1%, such as at least 2%, such as at least 3%, such as at least 4%, such as at least 5%, such as at least 6%, such as at least 7%, such as at least 8%, such as at least 9%, such as at least 10%, such as at least 20%, such as at least 30%, such as at least 40%, such as at least 50%, such as at least 60%, such as at least 70%, such as at least 80%, such as at least 90%, such as 100%, such as at least 200%, such as at least 300%, such as at least 400%, such as at least 500%, as may be measured in a cytokine production assay.

Embodiment 7: The monoclonal antibody according to any one of embodiments 1-6, which is capable of reducing the interferon-gamma (INF-γ) production of CD161-expressing cells by at least 1%, such as at least 2%, such as at least 3%, such as at least 4%, such as at least 5%, such as at least 6%, such as at least 7%, such as at least 8%, such as at least 9%, such as at least 10%, such as at least 20%, such as at least 30%, such as at least 40%, such as at least 50%, such as at least 60%, such as at least 70%, such as at least 80%, such as at least 90%, such as 100%, as may be measured in a cytokine production assay.

Embodiment 8: The monoclonal antibody according to any one of embodiments 1-7, wherein the $K_D$ of said mAB with LLT1 is $1\times10^{-8}$M or less, such as $1\times10^{-9}$M or less, such as $1\times10^{-19}$M or less, such as $1\times10^{-11}$M or less, such as $1\times10^{-12}$M or less.

Embodiment 9: The monoclonal antibody according to embodiment 8, wherein the $K_D$ of said mAb with LLT1 is at least 2-fold, such as at least 3-fold, such as at least 4-fold, such as at least 5-fold, such as at least 10-fold less than the $K_D$ of said mAb with another lectin of the C-type lectin superfamily.

Embodiment 10: The monoclonal antibody according to embodiment 9, wherein said lectin is CLEC2A, AICL or CD69.

Embodiment 11: The monoclonal antibody according to any one of embodiments 1-10, wherein the heavy chain of said antibody comprises:

a CDR1 sequence of amino acids 31 to 35 (SYGMS) of SEQ ID NO:4, wherein one of these amino acids may be substituted by a different amino acid; and/or a CDR2 sequence of amino acids 50 to 66 (TINSNGGRTFYPDSVKG) of SEQ ID NO:4, wherein one, two or three of these amino acids may be substituted by a different amino acid; and/or a CDR3 sequence of amino acids 99 to 108 (DGGYWAHFDY) of SEQ ID NO:4, wherein one, two or three of these amino acids may be substituted by a different amino acid.

Embodiment 12: The monoclonal antibody according to any one of embodiments 1-11, wherein the light chain of said antibody comprises:

a CDR1 sequence of amino acids 24 to 40 (RSSQSIVHSNGNTYLE) of SEQ ID NO: 7, wherein one, two or three of these amino acids may be substituted with a different amino acid; and/or a CDR2 sequence of amino acids 56 to 62 (KVSNRFS) of SEQ ID NO: 7, wherein one or two of these amino acids may be substituted with a different amino acid; and/or a CDR3 sequence of amino acids 94 to 102 (FQGSHVPWT) of SEQ ID NO: 7, wherein one or two of these amino acids may be substituted with a different amino acid.

Embodiment 13: The monoclonal antibody according to any one of embodiments 1-12, wherein the heavy chain of said antibody comprises:

a CDR1 sequence of amino acids 31 to 35 (SYGMS) of SEQ ID NO:4, wherein one of these amino acids may be substituted by a different amino acid; and/or a CDR2 sequence of amino acids 50 to 66 (TINSNGGRTFYPDSVKG) of SEQ ID NO:4, wherein one, two or three of these amino acids may be substituted by a different amino acid; and/or a CDR3 sequence of amino acids 99 to 108 (DGGYWAHFDY) of SEQ ID NO:4, wherein one, two or three of these amino acids may be substituted by a different amino acid.

and wherein the light chain of said antibody comprises:

a CDR1 sequence of amino acids 24 to 40 (RSSQSIVHSNGNTYLE) of SEQ ID NO: 7, wherein one, two or three of these amino acids may be substituted with a different amino acid; and/or a CDR2 sequence of amino acids 56 to 62 (KVSNRFS) of SEQ ID NO: 7, wherein one or two of these amino acids may be substituted with a different amino acid; and/or a CDR3 sequence of amino acids 94 to 102 (FQGSHVPWT) of SEQ ID NO: 7, wherein one or two of these amino acids may be substituted with a different amino acid.

Embodiment 14: The monoclonal antibody according to embodiment 13, wherein the heavy chain of said antibody comprises:

a CDR1 sequence of amino acids 31 to 35 (SYGMS) and
a CDR2 sequence of amino acids 50 to 66 (TINSNGGRTFYPDSVKG) and
a CDR3 sequence of amino acids 99 to 108 (DGGYWAHFDY) of SEQ ID NO:4; and wherein the light chain of said antibody comprises:
a CDR1 sequence of amino acids 24 to 40 (RSSQSIVHSNGNTYLE) and
a CDR2 sequence of amino acids 56 to 62 (KVSNRFS) and
a CDR3 sequence of amino acids 94 to 102 (FQGSHVPWT) of SEQ ID NO: 7.

Embodiment 15: The monoclonal antibody according to any one of embodiments 1-13, wherein the light chain of said antibody comprises SEQ ID NO: 7 and the heavy chain of said antibody comprises SEQ ID NO: 4.

Embodiment 16: A monoclonal antibody that is capable of binding LLT1, wherein the heavy chain of said antibody comprises:

a CDR1 sequence of amino acids 31 to 35 (DYYMH) of SEQ ID NO:10, wherein one of these amino acids may be substituted by a different amino acid; and/or a CDR2 sequence of amino acids 50 to 66 (WIDPENGDTEYAPKFQG) of SEQ ID NO:10, wherein one, two or three of these amino acids may be substituted by a different amino acid; and/or a CDR3 sequence of amino acids 98 to 109 (EIITTTAWFTY) of SEQ ID NO:10, wherein one, two or three of these amino acids may be substituted by a different amino acid.

Embodiment 17: A monoclonal antibody that is capable of binding LLT1, wherein the light chain of said antibody comprises:

a CDR1 sequence of amino acids 24 to 40 (KSSQSLLYTNGKTYLNW) of SEQ ID NO: 13, wherein one, two or three of these amino acids may be substituted with a different amino acid; and/or a CDR2 sequence of amino acids 56 to 62 (VSKLDSG) of SEQ ID NO: 13, wherein one or two of these amino acids may be substituted with a different amino acid; and/or a CDR3 sequence of amino acids 94 to 102 (LQNTHFPHT) of SEQ ID NO: 13, wherein one or two of these amino acids may be substituted with a different amino acid.

Embodiment 18: The monoclonal antibody according to any one of embodiments 8-10 and 16-17, wherein the heavy chain of said antibody comprises:

a CDR1 sequence of amino acids 31 to 35 (DYYMH) of SEQ ID NO:10, wherein one of these amino acids may be substituted by a different amino acid; and/or a CDR2 sequence of amino acids 50 to 66 (WIDPENGDTEYAPKFQG) of SEQ ID NO:10, wherein one, two or three of these amino acids may be substituted by a different amino acid; and/or a CDR3 sequence of amino acids 98 to 109 (EIITTTAWFTY) of SEQ ID NO:10, wherein one, two or three of these amino acids may be substituted by a different amino acid;

and wherein the light chain of said antibody comprises:

a CDR1 sequence of amino acids 24 to 40 (KSSQSLLYTNGKTYLNW) of SEQ ID NO: 13, wherein one, two or three of these amino acids may be substituted with a different amino acid; and/or a CDR2 sequence of amino acids 56 to 62 (VSKLDSG) of SEQ ID NO: 13, wherein one or two of these amino acids may be substituted with a different amino acid; and/or a CDR3 sequence of amino acids 94 to 102 (LQNTHFPHT) of SEQ ID NO: 13, wherein one or two of these amino acids may be substituted with a different amino acid.

Embodiment 19: The monoclonal antibody according to any one of embodiments 8-10 and 16-18, wherein the heavy chain of said antibody comprises:

a CDR1 sequence of amino acids 31 to 35 (DYYMH) and
a CDR2 sequence of amino acids 50 to 66 (WIDPENGDTEYAPKFQG) and
a CDR3 sequence of amino acids 98 to 109 (EIITTTAWFTY) of SEQ ID NO:10; and wherein the light chain of said antibody comprises:
a CDR1 sequence of amino acids 24 to 40 (KSSQSLLYTNGKTYLNW) and a CDR2 sequence of amino acids 56 to 62 (VSKLDSG) and a CDR3 sequence of amino acids 94 to 102 (LQNTHF-PHT) of SEQ ID NO: 13.

Embodiment 20: The monoclonal antibody according to any one of embodiments 8-10 and 16-19, wherein the light chain of said antibody comprises SEQ ID NO: 13 and the heavy chain of said antibody comprises SEQ ID NO: 10.

Embodiment 21: The monoclonal antibody according to any one of embodiments 1-20, which is a humanized antibody.

Embodiment 22: The monoclonal antibody according to any one of embodiments 1-20, which is a human antibody.

Embodiment 23: The monoclonal antibody according to any one of embodiments 1-20, which is a chimeric antibody.

Embodiment 24: The monoclonal antibody according to any one of embodiments 1-23, wherein the isotype of said antibody is an IgG.

Embodiment 25: The monoclonal antibody according to embodiment 24, wherein said isotype is IgG1.

Embodiment 26: The monoclonal antibody according to embodiment 24, wherein said isotype is IgG2.

Embodiment 27: The monoclonal antibody according to embodiment 24, wherein said isotype is IgG4.

Embodiment 28: A fragment of the monoclonal antibody according to any one of embodiments 1-27, which is a Fab, Fab', F(ab)2, F(ab')2, F(ab)S, Fv, single-chain Fv, dsFv, Fd or a dAb fragment, a VH, VL, VhH, or V-NAR domains, a monovalent molecule, minibody, diabody, triabody, tetrabody or kappa body, or an IgNAR.

Embodiment 29: A variant of the monoclonal antibody according to any one of embodiments 1-28, which is a deletion variant or an insertion variant.

Embodiment 30: A nucleic acid construct that encodes the monoclonal antibody according to any one of embodiments 1-29.

Embodiment 31: A recombinant vector that comprises the nucleic acid construct of embodiment 30.

Embodiment 32: An isolated cell that expresses the antibody according to any one of embodiments 1-29.

Embodiment 33: An isolated cell that comprises the nucleic acid construct of embodiment 30 or the vector of embodiment 31.

Embodiment 34: The cell according to embodiment 33, which is mammalian.

Embodiment 35: The cell according to embodiment 34, which is a HEK, a CHO or a BHK cell.

Embodiment 36: A pharmaceutical formulation comprising the monoclonal antibody according to any one of embodiments 1-29.

Embodiment 37: Use of the monoclonal antibody according to any one of embodiments 1-29 for the manufacture of a medicament.

Embodiment 38: The monoclonal antibody according to any one of embodiments 1-29 for the treatment of an autoimmune disease and/or chronic inflammation.

Embodiment 39: The monoclonal antibody according to any one of embodiments 1-29 for the treatment of is systemic lupus erythematosus (SLE).

Embodiment 40: The monoclonal antibody according to any one of embodiments 1-29 for the treatment of psoriasis.

Embodiment 41: The monoclonal antibody according to any one of embodiments 1-29 for the treatment of rheumatoid arthritis (RA).

Embodiment 42: The monoclonal antibody according to any one of embodiments 1-29 for the treatment of inflammatory bowel disease (IBD) and/or ulcerative colitis (UC) and/or Crohn's disease (CD).

Embodiment 43: The monoclonal antibody according to any one of embodiments 1-29 for the treatment of type 1 diabetes (T1D).

Embodiment 44: The monoclonal antibody according to any one of embodiments 1-29 for the treatment of cancer.

Embodiment 45: The monoclonal antibody according to any one of embodiments 1-29 for the treatment of B-cell lymphoma.

Embodiment 46: A method of treating an autoimmune disease and/or chronic inflammation, said method comprising administering a therapeutically or prophylactically effective amount of the monoclonal antibody according to any one of embodiments 1-29 to an individual in need thereof.

Embodiment 47: The method according to embodiment 46, wherein said autoimmune disease and/or chronic inflammation is systemic lupus erythematosus (SLE).

Embodiment 48: The method according to embodiment 46, wherein said autoimmune disease and/or chronic inflammation is psoriasis.

Embodiment 49: The method according to embodiment 46, wherein said autoimmune disease and/or chronic inflammation is rheumatoid arthritis (RA).

Embodiment 50: The method according to embodiment 46, wherein said autoimmune disease and/or chronic inflammation is inflammatory bowel disease (IBD) and/or ulcerative colitis (UC) and/or Crohn's disease (CD).

Embodiment 51: The method according to embodiment 46, wherein said autoimmune disease and/or chronic inflammation is type 1 diabetes (T1D).

Embodiment 52: A method of treating cancer, said method comprising administering a therapeutically or prophylactically effective amount of the monoclonal antibody according to any one of embodiments 1-29 to an individual in need thereof.

Embodiment 53: The method according to embodiment 52, wherein said cancer is B-cell lymphoma.

The invention is further illustrated by the following examples which are not to be construed as limiting the scope of protection. The features disclosed in the foregoing description and in the following examples may, both separately and in any combination thereof, be material for realising the invention in its diverse forms.

EXAMPLES

Cells over-expressing LLT-1 and LLT-Fc fusion protein were used to immunize mice. Monoclonal antibodies specific for LLT-1 were identified by screening for mAbs that could bind LLT-1 transfected cells, but not to cells lacking LLT-1. In a series of assays, LLT-1 specific mAb's were identified that 1) blocked binding of soluble LLT-1 to CD161 expressing cells, and 2) could augment the killing of LLT-1 expressing cells by CD161 expressing lymphocytes and augment IFNγ-production by NK cells. The anti-LLT1 antibodies were used to demonstrate the expression of LLT1 on the surface of activated, but not resting dendritic cells (DC's) and T, NK- and B lymphocytes. Moreover, the anti-LLT1 antibodies were used to demonstrate expression of LLT1 in inflamed tissue from patients with inflammatory bowel diseases (Crohn's disease and ulcerative colitis) and rheumatoid arthritis, and in cancer cells from B cell lymphomas.

Examples 1 and 2

Examples 1 and 2 describe the generation, characterization, cloning and recombinant expression of anti-LLT1 antibodies anti-LLT14F and anti-LLT12F1A5.

Example 1

Production and Characterization of Monoclonal Antibodies Directed Against LLT1

Monoclonal antibodies were generated against lectin-like transcript-1 (LLT-1, SEQ ID NO:1). Monoclonal antibodies having the desired binding specificity were identified, cloned and sequenced. Selected anti-LLT1 antibodies were characterized for functional activity. One of the antibodies was found to block LLT-1 binding to its receptor, CD161, and to inhibit LLT-1 induced CD161 activity.

Methods and Results
Immunization and Fusion

RBF-mice were immunized three times with 5xE6 LLT1-expressing HeLa cells or with LLT1-hFc fusion protein in CFa/IFA. Generation of LLT1 expressing cells and LLT1-hFc fusion proteins were described by Aldemir et al 2005. Ten days after the last immunization, eye-bleeds from immunized mice were screened in FACS and ELISA for LLT1-specific antibodies. Mice with positive titers were boosted with 10 µg of soluble LLT1-hFc fusion protein, by intravenous injection, and sacrificed after three days. The spleen was removed aseptically and dispersed to a single cell suspension. Fusion of spleenocytes and FOX-NY myeloma cells was done by the PEG-fusion method. Cells were seeded in microtiter plates and cultured at 37° C., 5% $CO_2$. The tissue-culture medium containing AAT for selection was changed three times over a two week's period.

Primary Screening of Hybridomas

Hybridoma's derived from immunized RBF-mice were screened for production of LLT1-specific Mab's, by testing their tissue-culture supernatants for recognition of LLT1-positive cells by flow-cytometry and ELISA.

Flow-Cytometry

Tissue-culture supernatants were incubated with HEK293 cells expressing LLT1 (Aldemir et al 2005). After incubation on ice for an hour, cells were washed with DMEM/2% FCS, and incubated with APC-conjugated donkey anti-mouse secondary Ab-fragments, for half an hour on ice. After extensive washing with PBS, Ab-binding to living cells was analyzed using FACS.

ELISA

Tissue-culture supernatants were tested for LLT1 MAb's in a direct ELISA-assay, For this, Nunc immunoplates were coated with 1 µg/ml of LLT1-hFc protein (Aldemir et al 2005) in PBS and incubated overnight at 4° C. Plates were blocked with blocking buffer (PBS with 0.05% Tween-20) for 15 min and were washed with PBS/0.05% Tween-20. Culture supernatants from the hybridoma cells were added and the plates were incubated for 1 hour at room temperature. After another wash HRPO labelled goat anti-mouse IgG-specific Ab's (1:2000 diluted, Caltac, Ca) was added followed by another hour of incubation. Plates were washed and developed with TMB-substrate (Kem-EN-Tec), as described by the manufacturer. Absorbance at 450 nm was measured on an ELISA-reader, which was directly coupled to 96-wells plates.

Subcloning of Selected Hybridomas

In order to generate a monoclonal and stable hybridoma, cells were subcloned using limited dilution method. Cells were seeded into a 96 well plates by a density of 1 cell/well. After two weeks, supernatants from each well were screened in a direct ELISA. Cells from positive wells were transferred to a larger culture volume and expanded.

Antibody Cloning and Sequencing

Murine heavy chain and light chain sequences for anti-LLT1 antibodies were cloned from the hybridomas: anti-LLT12F1A5 and anti-LLT14F. Total RNA, extracted from hybridoma cells using the RNeasy-Mini Kit from Qiagen, was used as templates for cDNA synthesis. cDNA was synthesized in a 5'-RACE reaction using the SMART™ RACE cDNA amplification kit from Clontech. Subsequent target amplification of HC and LC sequences was performed by PCR using Phusion Hot Star polymerase (Finnzymes) and the universal primer mix (UPM) included in the SMART™ RACE kit as a for-ward primer. A reverse primer with the following sequence was used for HC (VH domain) amplification: 5'-CCCTTGACCAGGCATCCCAG-3' (primer #129). A reverse primer with the following sequence was used for LC amplification: 5'-GCTCTAGACTAACACTCATTCCTGTTGAAGCTC-3' (primer #71).

PCR products were separated by gel electrophoresis, extracted using the GFX PCR DNA and Gel Band Purification Kit from GE Healthcare Bio-Sciences and cloned for sequencing using a Zero Blunt TOPO PCR Cloning Kit and chemically competent TOP10 E. coli from Invitrogen. Colony PCR was performed on selected colonies using an AmpliTaq Gold Master Mix from Applied Biosystems and 13uni/M13rev primers. Colony PCR clean-up was performed using the ExoSAP-IT enzyme mix (USB). Sequencing was performed at MWG Biotech, Martinsried Germany using either T3/T7 sequencing primers. Sequences were analyzed and annotated using the VectorNTI program.

From each hybridoma, anti-LLT12F1A5 and anti-LLT14F, respectively, a single unique murine LC type kappa was identified and a single unique murine HC, subclass IgG1.

BLAST Searches

The translated anti-LLT12F1A5 and anti-LLT14F VL and VH amino acid sequences were used as query sequences. BLAST searches were performed against sequences in the Uniprot database using the BLASTp translations program (detailed data missing from SBP).

In conclusion, the VH and VL sequences for anti-LLT12F1A5 and anti-LLT14F represent new unique sequences.

Biacore Analysis of Anti-LLT12F1A5

The kinetic parameters for the interaction of anti-LLT12F1A5 with LLT1 were evaluated by Biacore analysis.

Surface plasmon resonance measurements were performed on a Biacore T100 apparatus (Biacore) at 25° C. In all Biacore experiments, HBS buffer supplemented with 0.05% surfactant P20 served as running buffer and sensorgrams were analyzed with Biaevaluation software. Recombinant LLT1-Fc fusion protein (described by Aldemir et al in Journal of Immunology, 2005 vol. 176: 7791-7795) were immobilized covalently to carboxyl groups in the dextran layer on a Sensor Chip CM5 (Biacore). The sensor chip surface was activated with EDC/NHS(N-ethyl-N'-(3-dimethylaminopropyl) carbodiimidehydrochloride and N-hydroxysuccinimide, Biacore). Proteins diluted in coupling buffer (10 mM acetate, pH 4.5) were injected. Deactivation of the remaining activated groups was performed using 100 mM ethanolamine pH 8 (Biacore).

Anti-LLT12F1A5 was tested in a range of concentrations from 3.125 to 100 nM for binding to immobilized LLT1-Fc protein (500 RU). The binding affinity of anti-LLT12F1A5 was found to be $1.24 \times 10^{-9}$ M.

Western Blot Analysis

Protein was extracted from C1R-LLT1 and 293T-LLT1 transfectants and corresponding parental cell lines and separated by SDS-polyacrylamide gel electrophoresis under reducing (R) or non-reducing (NR) conditions. A molecular weight marker was run in parallel in the same gel. The separated proteins were blotted onto filter and stained with anti-LLT12F1 and mAb4C7 antibodies according to standard procedure.

Anti-LLT12F1 staining revealed bands of ~33-35 and 66-70 kDa under reducing and non-reducing conditions, respectively (FIG. 3). These protein/protein-complexes were present in proteins extracts from C1R— and 293T-LLT1 cells, but absent in protein extract from parental C1R and 293T cells. Immunoblotting of 293T-LLT1 cell extract with mAb4C7 antibody confirmed these data (FIG. 3B). In conclusion, the molecular weight of monomeric glycosylated LLT1 is ~35 kDa and LLT1 is expressed as a homodimer.

Flow Cytometry

Figure 4:
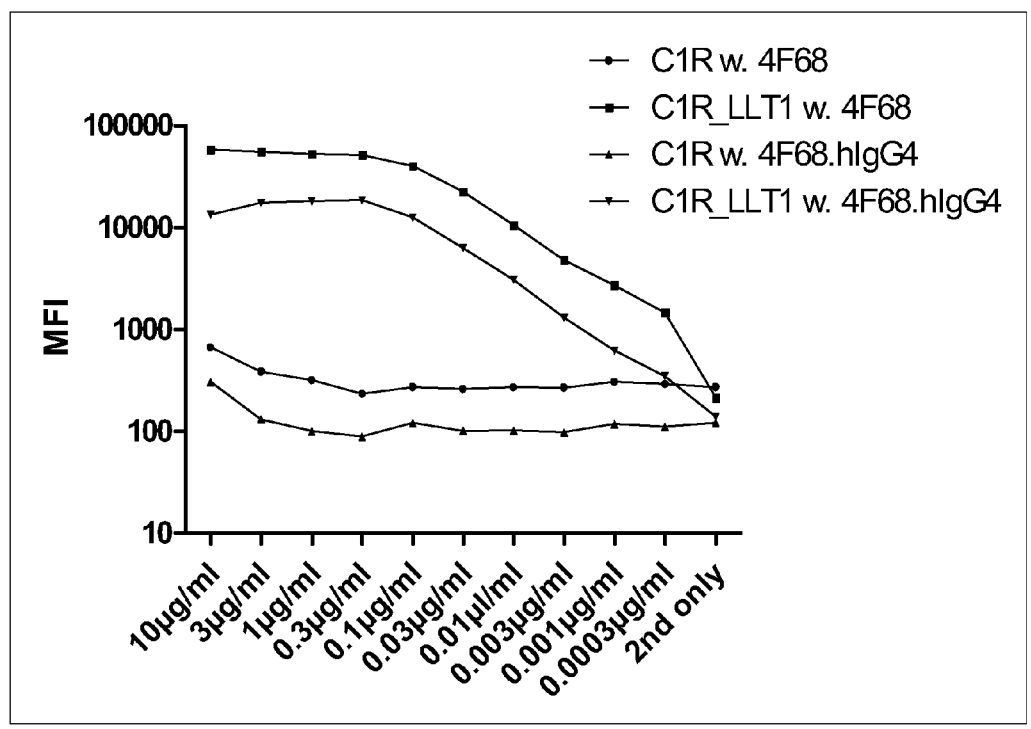
FIG. 4 shows dose-dependent binding of both mouse and chimeric mouse/human mAb, anti-LLT14F, to LLT1.

C1R-LLT1 transfectants and parental C1R cells were washed in PBS containing 1% FCS and incubated with anti-LLT14F or anti-LLT14F-hIgG4 antibody at concentrations 0.0003-10 μg/ml as indicated in FIG. 4 for 30 min at 4° C. followed by incubation with fluorochrome-conjugated anti-mouse or anti-human IgG secondary antibodies, respectively. Samples were washed three times in PBS containing 1% FCS and analysed by flow cytometry.

As shown in FIG. 4, anti-LLT14F and anti-LLT14F-hIgG4 bound concentration-dependently to C1R-LLT1 cells, but not to untransfected C1R cells. In conclusion, both mouse and chimeric mouse/human anti-LLT14F antibodies were able to recognize and bind to recombinantly expressed LLT1 on the cell surface of C1R cells.

LLT1-Multimer Binding to 293T-CD161 Transfectants

A multimeric complex was generated by incubating the LLT1-Fc fusion protein with biotinylated protein A (Pierce) at a molar ratio of 1:1. Saturating amounts of purified hIgG were added to block the remaining free protein A sites. A multimer control was generated using protein A-biotin saturated with purified hIgG. These complexes were conjugated to streptavidin-allophycocyanin (BD Biosciences). Ten micrograms of LLT1- and Ctrl-hIgG-multimers was incubated for 45 min at 4° C. with $2 \times 10^5$ 293T-CD161 cells. Anti-LLT14F (4F) or control IgG1 (ctrl IgG1) was added at concentrations 0.01-200 μg/ml. For comparison, anti-LLT12F1 (2F1A5) and AF3480 were tested in parallel with 4F in this assay. Binding of LLT1-multimers was evaluated by flow cytometry.

As shown in FIG. 5A, binding of LLT1-multimers to CD161 transfectants was reduced dose-dependently by anti-LLT14F, but not by isotype control antibody. Anti-LLT14F completely abolished LLT1-multimer binding at concentrations 20 μg/ml. In addition, only anti-LLT14F but not anti-LLT12F1 (2F1A5), 4C7 and MAB3480 antibodies block the LLT1-induced downregulation of CD161 on the cell surface of NK cells incubated with LLT1-expressing cells (FIG. 5B). These data demonstrate that anti-LLT14F blocks the interaction between LLT1 and CD161.

NK Cell Cytotoxicity Assay (described in detail example 5)

NK Cell IFNg Production (described in detail example 5)

Example 2

Cloning and Sequencing of Mouse Anti-LLT12F1A5 and Anti-LLT14F mAb's

This example describes cloning and sequencing of the murine heavy chain and light chain sequences of anti-LLT1 antibodies: anti-LLT12F1A5 and anti-LLT14F. Four anti-LLT14F hybridomas (4F2, 4F8, 4F46, 4F68) carried antibodies with the same CDR sequence and therefore produced identical antibodies.

Total RNA was extracted from hybridoma cells using the RNeasy-Mini Kit from Qiagen and used as template for cDNA synthesis. cDNA was synthesized in a 5'-RACE reaction using the SMART™ RACE cDNA amplification kit from Clontech. Subsequent target amplification of HC and LC sequences was performed by PCR using Phusion Hot Start polymerase (Finnzymes) and the universal primer mix (UPM) included in the SMART™ RACE kit as forward primer. The reverse primer 5'-CCCTTGACCAGGCATC-CCAG-3' was used for HC (VH domain) amplification and the reverse primer 5'-GCTCTAGACTAACACTCATTCCT-GTTGAAGCTC-3' was used for LC amplification. PCR products were separated by gel electrophoresis, extracted using the GFX PCR DNA & Gel Band Purification Kit from GE Healthcare Bio-Sciences and cloned for sequencing using a Zero Blunt TOPO PCR Cloning Kit and chemically competent TOP10 *E. coli* (Invitrogen). Colony PCR was performed on selected colonies using an AmpliTaq Gold Master Mix from Applied Biosystems and M13uni/M13rev primers. Colony PCR clean-up was performed using the ExoSAP-IT enzyme mix (USB). Sequencing was performed at MWG Biotech, Martinsried Germany using either T3/T7 sequencing primers. Sequences were analyzed and annotated using the VectorNTI program. All kits and reagents were used according to the manufacturer's instructions.

A single unique murine LC type kappa and a single unique murine HC, subclass IgG1 was identified for each hybridoma.

Generation of Mouse Anti-LLT14F Expression Vectors

A series of CMV promotor-based expression vectors (pTT vectors) were generated for transient expression of the mouse anti-LLT14F antibody in the HEK293-6E EBNA-based expression system developed by Yves Durocher (Durocher et al. Nucleic Acid Research, 2002). In addition to the CMV promotor, the vectors contain a pMB1 origin, an EBV origin and the Amp resistance gene. The region corresponding to the full length anti-LLT14F LC (including the original signal peptide sequence) was PCR amplified from the original TOPO sequencing clones using primers specific for the N and C-terminal sequences. The sense primer contained a terminal HindIII restriction site sequences for cloning purposes and a Kozak sequence (5'-GCCGCCACC-3') immediately upstream of the ATG start codon. The anti-sense primer contained a stop codon followed by an XbaI restriction site sequence, immediately downstream of the coding sequence. The generated PCR fragment was restriction digested, cloned into the multiple cloning site (MCS) of a linearized pTT-based vector and transformed into *E. coli* for selection. The sequence of the final construct was verified by DNA sequencing.

The region corresponding to the VH domain (including the original signal peptide sequence) was PCR amplified from the original TOPO sequencing clones using primers specific for the N-terminal sequence and VH/CH transition sequence. The sense primer contained a terminal NotI restriction site sequences for cloning purposes and a Kozak sequence (5'-GCCGCCACC-3') immediately upstream of the ATG start codon. The anti-sense primer contained an in-frame NheI restriction site downstream of the VH/CH transition. The generated VH domain PCR fragment was restriction digested, cloned into a linearized vector containing the CH domain sequence for a murine IgG1 and transformed into *E. coli* for selection. The sequence of the final construct was verified by DNA sequencing. The cloned and recombinant expressed anti-LLT14F antibody had the same profile and affinity in all assay used, as the original hybridoma derived antibody.

Generation of Expression Vectors for Mouse/Human Chimeric Anti-LLT14F

To enable the best possible evaluation of anti-LLT14F, a mouse/human chimera version of the anti-LLT14F antibody (ChimLLT14F) was constructed in order to eliminate any differences related to constant region origin and isotype. pTT-based expression vectors were generated for transient expression of chimeric anti-LLT14F antibody with murine variable domains on either the human kappa/IgG1 or kappa/IgG4 (S241P) isotype scaffolds. The proline mutation at position 241 (numbering according to Kabat, corresponding to residue 228 per the EU numbering system (Edelman G. M. et AL., Proc. Natl. Acad. USA 63, 78-85 (1969)) was introduced in the IgG4 hinge region to eliminated formation of monomeric antibody fragments, i.e. "half-antibodies" comprising of one LC and one HC. The region corresponding to the VH domain was PCR amplified from a anti-LLT14F68A3 HC expression plasmid using a generic pTT specific primer and a primer specific for the VH domain C-terminus. The sense primer is specific for at sequence stretch upstream of the HindIII restriction site and the ATG start codon. The anti-sense primer contained an in-frame NheI restriction site in the VH/CH transition sequence. The generated PCR fragment was restriction digested, cloned into a linearized pTT-based vector containing the sequence for a human IgG4 (S241P)CH domain and subsequently transformed into *E. coli* for selection. The sequence of the final construct was verified by DNA sequencing. The region corresponding to the VL domain was PCR amplified from a anti-LLT14F LC expression plasmid using a generic pTT specific primer and a primer specific for the VL domain C-terminus. The sense primer is specific for at sequence stretch upstream of the HindIII restriction site and the ATG start codon. The anti-sense primer contained an in-frame BsiWI restriction site in the VL/CL transition sequence. The generated PCR fragment was restriction digested, cloned into a linearized pTT-based vector containing the sequence for a human kappa CL domain and subsequently transformed into *E. coli* for selection. The sequence of the final construct was verified by DNA sequencing.

Recombinant Expression of mAb Variants

The murine anti-LLT14F and the chimeric anti-LLT14F antibodies were expressed transiently in HEK293-6E cells following a generic antibody expression protocol. The following procedure describes the generic transfection protocol used for suspension adapted HEK293-6E cells.

Cell Maintenance

HEK293-6E cells were grown in suspension in FreeStyle™ 293 expression medium (Gibco) supplemented with 25 µg/ml Geneticin (Gibco), 1% v/v of the surfactant Pluronic F-68 (Gibco) and 1% v/v Penicillin-Streptomycin (Gibco). Cells were cultured in Erlenmeyer shaker flasks in shaker incubators at 37° C., 8% CO2 and 125 rpm and maintained at cell densities between $0.1-1.5 \times 10^6$ cells/ml.

DNA Transfection

The cell density of cultures used for transfection was $0.9-1.1 \times 106$ cells/ml.

A mix of 0.5 µg LC vector DNA+0.5 µg HC vector DNA was used per ml cell culture.

The DNA was diluted in Opti-MEM media (Gibco) 30 µl media/µg DNA, mixed and incubated at room temperature (23-25° C.) for 5 min.

293Fectin™ (Invitrogen) was used as transfection reagent at a concentration of 1 µl per µg DNA.

The 293Fectin™ was diluted 30× in Opti-MEM media (Gibco), mixed and incubated at room temperature (23-25° C.) for 5 min.

The DNA and 293Fectin solutions were mixed and left to incubate at room temperature (23-25° C.) for 25 min.

The DNA-293Fectin mix was then added directly to the cell culture.

The transfected cell culture was transferred to a shaker incubator at 37° C., 8% CO2 and 125 rpm.

3-6 days post transfection, cell culture supernatants were harvested by centrifugation, followed by filtration through a 0.22 µm PES filter (Corning).

Quantitative analysis of antibody production was performed by Biolayer Interferometry directly on clarified cell culture supernatants using the ForteBio Octet system and protein A biosensors or quantitative protein A HPLC.

Examples 3 to 5

Examples 3-5 describe the binding specificity and functional activity of mAbs anti-LLT14F and anti-LLT12F1A5 compared to that of two commercial available anti-LLT1 monoclonal antibodies, MAB3480 and 4C7.

Example 3

Comparison of Anti-LLT12F1A5 and Anti-LLT14F with mAb's 4C7 and MAB3480 in the ELISA Application Anti-LLT12F1A5 and anti-LLT14F were compared to mAb's 4C7 and MAB3480 with respect to binding to CLEC2D (LLT1) fusion proteins in the ELISA application. Wells were coated with Fc fusion proteins representing full-length CLEC2D or splice variant 2 and 4 hereof (CLEC2D-iso2 and -iso4, respectively). Full-length CLEC2D contains exons 1, 2, 3, 4a and 5, whereas isoforms 2 and 4 contain exons 1, 2, 3, 4a, 4b, 5 and exons 1, 2, 3, 5, respectively. Coated wells were incubated with anti-LLT12F1A5, anti-LLT14F, MAB3480 or 4C7 antibodies. Wells not coated with protein (PBS) or coated with CLEC2A-Fc protein were included as negative controls. Antibody binding was detected by HRP-conjugated anti-mouse Ig secondary antibody and chromogen. HRP-conjugated anti-human Ig antibody was included as a positive control that recognized the Fc portion of both fusion proteins. Data are presented in Table 1.

TABLE 1

ELISA-binding of anti-LLT1 antibodies to LLT1- and CLEC2A-Fc fusion proteins

| | | Secondary mAb Primary | + anti-mIg-HRP | | | | Anti-human Ig Fc- |
|---|---|---|---|---|---|---|---|
| OD | | mAb | PBS | 2F1 | 4F | MAB3480 | 4C7 | HRP |
| Coated proteins | PBS | | 0.08 | 0.086 | 0.081 | 0.083 | 0.084 | 0.08 |
| | LLT1-Fc | | 0.118 | 1.175 | 0.511 | 1.207 | 1.194 | 1.077 |
| | CLEC2A-Fc | | 0.096 | 0.114 | 0.103 | 0.104 | 1.172 | 1.153 |
| | CLEC2D iso2-Fc | | 0.102 | 0.105 | 0.111 | 0.117 | 1.033 | 1.01 |
| | CLEC2D iso4-Fc | | 0.092 | 0.094 | 0.093 | 0.112 | 1.008 | 1.045 |

Anti-LLT12F1A5, anti-LLT14F and MAB3480 bound to LLT1, but not to CLEC2A. These antibodies recognized full-length LLT1, but not isoforms 2 and 4. The binding profile of mAb 4C7 was markedly different, since this antibody recognized not only full-length LLT1, but also isoforms 2 and 4 and, moreover, bound to CLEC2A. These data demonstrate that mAb4C7 binds all three forms of LLT1 and cross-reacts with CLEC2A, whereas the three other antibodies recognize exclusively full-length LLT1. Therefore, the epitope recognized by mAb 4C7 is different from those recognized by anti-LLT12F1A5, anti-LLT14F and mAb3480.

Example 4

Comparison of Anti-LLT12F1A5 and Anti-LLT14F with mAbs 4C7 and MAB3480 in the Flow Cytometry Application Anti-LLT12F1A5 and anti-LLT14F was compared to mAb's 4C7 and MAB3480 for binding to a series of cells lines: untransfected C1R cells, C1R-LLT1 transfectants, Raji cells, U937 cells and U373 cells in the flow cytometry application. Moreover, binding of these antibodies to 293T cells transfected or not with LLT1 or AICL were analyses and compared to that of anti-AICL mAb 7G4. TNP IgG1 (mIgG1) was included as isotype control.

Figure 6A:
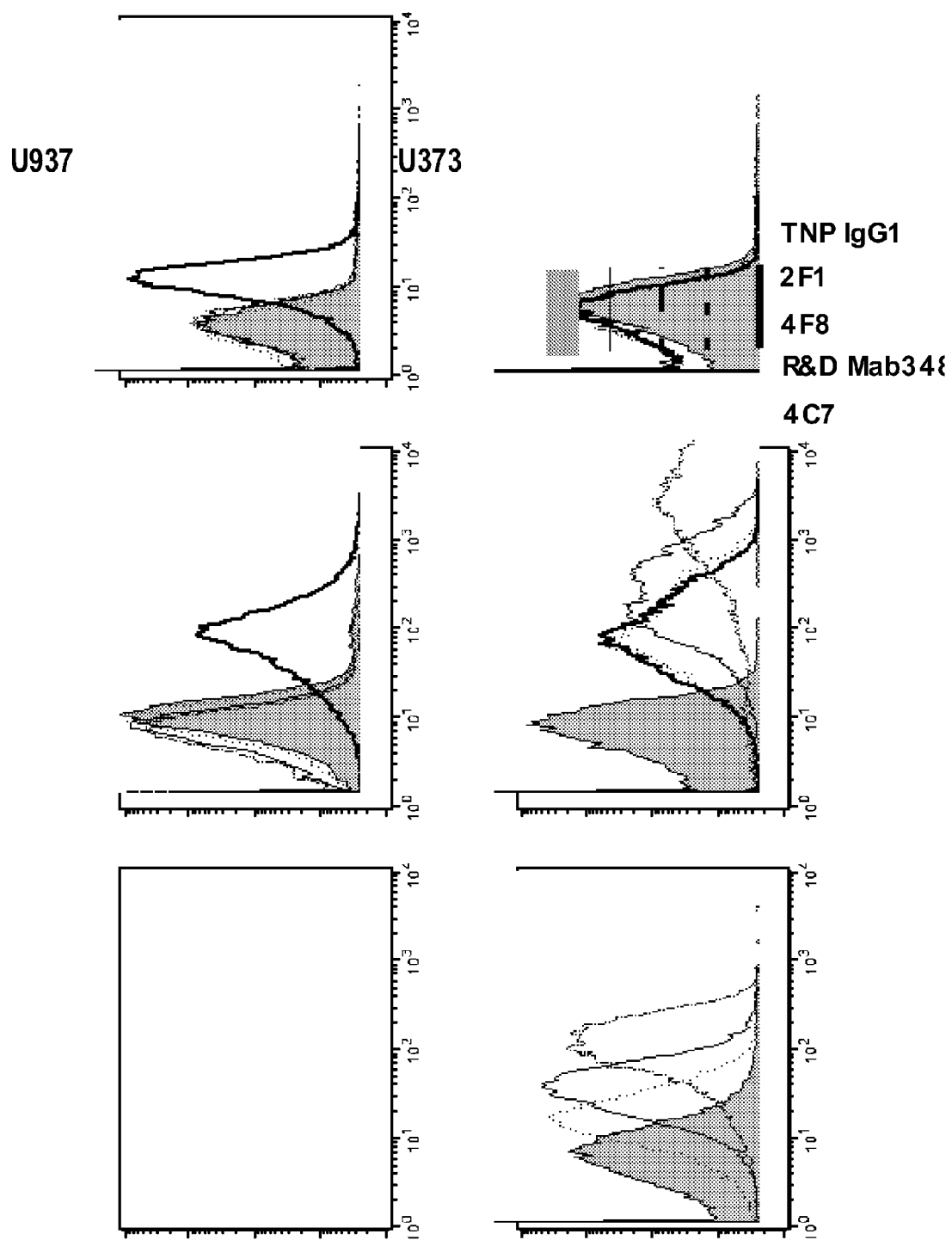
FIG. 6 shows binding of mAbs anti-LLT14F and anti-LLT2F1 compared to mab3480 and 4C7 to LLT1- and AICL-transfectants and to human tumor cell lines.
Figure 6B:
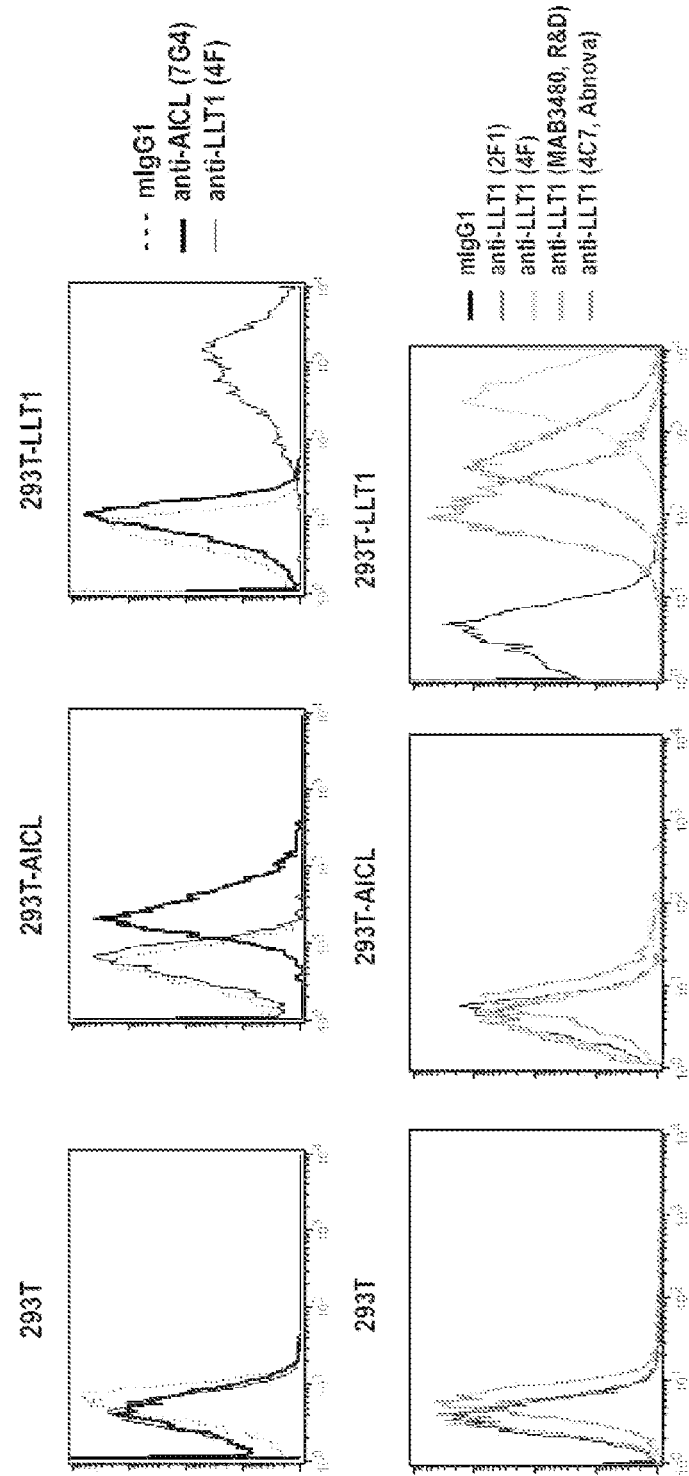

As shown in FIG. 6, all 4 anti-LLT1 antibodies bound to C1R- and 293T-LLT1 transfectants, but not to untransfected C1R or 293T cells. Cells transfected with AICL bound anti-AICL mAb 7G4, but not any of the 4 anti-LLT1 antibodies. Moreover, binding to Raji cells could be detected for anti-LLT12F1A5, anti-LLT14F and MAB3480, but not for mAb 4C7. In contrast, only mAb 4C7 bound U937 and U373 cells. These data demonstrate that anti-LLT12F1A5 and anti-LLT14F bind specifically to LLT1 without recognizing the closely related AICL. Moreover, the binding specificity of anti-LLT12F1A5 and anti-LLT14F was found to be different from that of mAb 4C7.

Example 5

Functional Activity of Anti-LLT12F1A5 and Anti-LLT14F Compared with MAB3480

Material and Methods

NK cells were incubated with C1R or C1R-LLT1 cells in the presence of the indicated mAbs: Anti-LLT2F1, anti-LLT14F (4F8, 4F46, 4F68), MAB3480 (R&D systems), AF3480 (R&D systems); anti-CD161 mAbs 191B8 (Beckman-Coulter), DX12 (BD Biosciences), HP3G10 (M. Lopez-Botet), anti-Human HLA-ABC DX17 (BD Pharmingen); isotype controls: TNP1 (mIgG1), TNP2a (mIgG2a), Iggoat (goat Ig). Anti-CD107a-PE was added at the beginning of the incubation and brefeldin A 1 h later. Cells were incubated at 37° C. for 5 h or 4 h before assessment of NK cell cytoxicity and IFN-γ production, respectively. NK cell cytoxicity was assessed by flow cytometry using cell surface staining of CD107a and IFN-γ production by NK cells was measured by flow cytometry intracellular staining. Data are presented in Table 2.

TABLE 2

Effect of anti-LLT1 antibodies on NK cell degranulation and IFNγ release in response to C1R-LLT1 cells

| | % CD107a+ NK cells | % IFN-γ+ NK cells |
|---|---|---|
| NK cells | 1.8 | 1.1 |
| NK cells + C1R | 13.3 | 5.2 |
| NK cells + C1R-LLT1 | 4.6 | 2.9 |
| NK cells + C1R-LLT1 + mIgG2a | 4.5 | 3.5 |
| NK cells + C1R-LLT1 + anti-CD161 (191B8) | 13.2 | 7.4 |
| NK cells + C1R-LLT1 + mIgG1 | 4.3 | 3.0 |
| NK cells + C1R-LLT1 + anti-CD161 (DX12) | 8.1 | 5.4 |
| NK cells + C1R-LLT1 + anti-CD161 (HP3G10) | 9.5 | 5.3 |
| NK cells + C1R-LLT1 + anti-LLT1 (MAB3480) | 4.7 | 3.0 |
| NK cells + C1R-LLT1 + anti-LLT1 (2F1) | 5.0 | 3.2 |
| NK cells + C1R-LLT1 + anti-LLT1 (4F) | 9.6 | 5.1 |
| NK cells + C1R-LLT1 + goatIgG | 4.5 | 4.8 |
| NK cells + CIR-LLT1 + anti-LLT1 (AF3480) | 5.3 | 3.3 |

Co-culture of NK cells with C1R cells induced NK cell-mediated cytotoxicity and IFNγ production. Recombinant expression of LLT1 by C1R cells inhibited NK cell-mediated cytotoxicity and IFN-γ production. Addition of 1 g control antibodies (TNP1, TNP2A or Iggoat) did not influence the LLT1-mediated inhibition. In contrast, anti-LLT14F (4F8 and 4F46 that have identical CDRs) partially blocked the LLT1-mediated inhibition. This effect could not be mimicked by anti-LLT12FA5, MAB3480 and AF3480. Three anti-CD161 antibodies (191B8, HP3G10 and DX12) fully or partially blocked the LLT1-mediated inhibition.

In conclusion, these data demonstrate that anti-LLT14F, but not other anti-LLT1 antibodies (anti-LLT12F1, MAB3480, AF3480) blocked the inhibitory effect of LLT1 on NK cell-mediated cytotoxicity and IFN-γ production.

Examples 6-8

Examples 6-8 describe the induction of LLT1 expression on PMBC-derived B and T lymphocytes and dendritic cells upon in vitro activation.

Example 6

Induction of LLT1 Surface Expression Upon Toll-Like-Receptor (TLR) Activation in Dendritic Cells (DC's) and B Cells CD19+ B cells and CD14+ monocytes were isolated from peripheral blood. B cells were cultured in plain medium or in medium supplemented with CL097 or ODN2216 that are agonists for the toll-like-receptors (TLRs) 7 and 9, respectively. Monocytes were differentiated to dendritic cells (DC's) in the presence of GM-CSF and IL-4 and cultured in the absence (immature DC's) or presence of the TLR4 agonist LPS alone or LPS and IFN-γ. Surface expression of LLT1 on B cells and DC's was evaluated by flow cytometry using biotinylated anti-LLT14F (4F68-B). Biotinylated mouse IgG1 (mIgG1-B) was included as negative isotype control antibody. Data are presented in Tables 3 and 4.

TABLE 3

Induction of LLT1 expression on DC's upon LPS treatment.

| Cell type and treatment | Antibodies | % of LLT1+ cells | x-mean |
|---|---|---|---|
| iDC's | mIgG1-B | 12.43 | 13.26 |
| | 4F68-B | 3.66 | 6.68 |
| DC's + LPS | mIgG1-B | 3.95 | 7.54 |
| | 4F68-B | 30.08 | 18.19 |
| DC's + LPS + IFNγ | mIgG1-B | 5.72 | 8.63 |
| | 4F68-B | 72.29 | 59.94 |

TABLE 4

Induction of LLT1 expression on B cells upon TLR7/9 agonist treatment.

| Cell type and treatment | Antibodies | % of LLT1+ cells | x-mean |
|---|---|---|---|
| B cells + medium | mIgG1-B | 2.66 | 7.95 |
| | 4F68-B | 9.77 | 13.75 |
| B cells + CL097 | mIgG1-B | 2.24 | 8.33 |
| | 4F68-B | 60.47 | 64.08 |
| B cells + CpG ODN 2216 | mIgG1-B | 1.26 | 6.62 |
| | 4F68-B | 39.40 | 44.07 |

LLT1 was not expressed on the surface of resting B cells or immature DC's, but was induced on B cells by TLR7 and TLR9 agonists CL097 and ODN2216, respectively, and on DC's by the TLR4 agonist LPS. The induction of LLT1 on DC's by LPS was potentiated by IFN-γ. These data demonstrate that LLT1 is expressed on the surface of activated, but not resting B cells and DC's.

Example 7

Induction of LLT1 on B Cells in Allogenic B-T Cell Mixed Lymphocyte Reaction (MLR)

Material and Methods
Cells

Human CD4+ T cells were purified from PBMC by negative selection (Stem Cell Technologies) followed by positive selection of the CD45RO+ memory T cell population (Miltenyi Biotec). Human B cells were purified from PBMC by negative selection (EasySep) and subsequently labelled with 5 uM CFSE (carboxyfluorescein diacetate succinimidyl ester) for 10 min at 37° C. in the dark in RPMI 1640 complete medium containing 2% FCS.

B-T Cell MLR

The purified CD4+/CD45RO+ T cells ($10^5$ cells/well) were cocultured in 96-well round-bottom plates with the CFSE-labelled allogenic B cells ($10^5$ cells/well) for 6 days (37° C., 5% $CO_2$) in 0.2 ml/well of RPMI 1640 complete medium containing 10% FCS. At day 6 cells were counter-stained with antibodies to cell surface markers (e.g. CD20, CD4, LLT1) and analysed by flow cytometry.

Flow-Cytometry

Cells were washed in PBS containing 1% FCS and incubated with relevant fluorochrome-conjugated antibody for 30 min at 4° C. Samples were washed three times in PBS containing 1% FCS and analysed by flow cytometry. Cells stained with biotinylated anti-LLT1-4F mIgG1 mAb were subsequently washed and incubated with streptavidin-APC for 30 min at 4° C. followed by washing prior to FACS analysis. Biotinylated mIgG1 was included as negative control. Data are expressed as MFI (median fluorescence intensity) and presented in Table 5.

Results

Staining of the B cells with CFSE allowed phenotypic analysis of the B cell population after 6 days T-B cell MLR, since CFSE stains intracellular proteins and segregates equally between daughter cells with each cell division. Analysis of the CFSE-labelled B cell population by flow cytometry showed that B cells had proliferated during the 6 days co-culture with allogenic T cells. The resting and the proliferating B cell populations were analysed for LLT1 surface expression using biotinylated mAb anti-LLT1-4F68 IgG1. Biotinylated mIgG1 served as negative control.

TABLE 5

LLT1 expression on proliferating B cells in allogenic T-B cell mixed lymphocyte reaction assay

| | Proliferating | LLT1 expression (MFI) | |
|---|---|---|---|
| Cells in culture | B cells (%) | Resting B cells | Proliferating B cells |
| B cells alone | 0 | 4 | N/A |
| B cells + T cells | 55 | 29 | 212 |

MFI (median fluorescence intensity) calculated as MFI (LLT1)−MFI (isotype control); NA not adequate.

LLT1 is up-regulated on proliferating B cells, whereas it is absent from the resting population of B cells. CFSE-labelled B cells incubated for 6 days in the absence of allogenic T cells do not proliferate and do not express LLT1 at the cell surface (Table 5). These data show that B cells up-regulate LLT1 on the cell surface upon activation by allogenic T cells in a MLR reaction.

Example 8

Induction of LLT1 Surface Expression on Activated T Cells

Material and Methods

Generation of Monocyte-Derived Immature DCs

Monocyte-derived DCs were generated by positive selection of CD14$^+$ monocytes from human PBMC using magnetic beads (Miltenyi Biotech). CD14$^+$ monocytes were cultured for 5 days in the presence of 40 ng/ml GM-CSF (Biosource) and 40 ng/ml IL-4 (R&D) in RPMI 1640 complete medium containing 10% FCS to generate immature DCs.

Generation of CD4$^+$ or CD4$^+$/CD45RO$^+$ T Cells

Human CD4$^+$ T cells were purified from PBMC by negative selection (Stem Cell Technologies) and used in the anti-CD3 activation assay. Alternatively, CD4$^+$ purification was followed by positive selection of the CD45RO$^+$ memory T cell population (Miltenyi Biotec) for MLR assay. In order to follow T cell proliferation, CD4$^+$ T cells or CD4$^+$/CD45RO$^+$ T cells were labelled with 5 μM CFSE for 10 min at 37° C. in the dark in RPMI 1640 complete medium containing 2% FCS.

Allogenic DC-T Cell MLR

The generated immature DCs were harvested at day 5 and co-cultured (at 2.5×10$^4$/well) with allogenic CFSE-labelled human CD4$^+$/CD45RO$^+$ T cells (at 2.5×10$^5$/well) in 96-well round-bottom plates for 6 days in 0.2 ml/well of RPMI 1640 complete medium containing 10% FCS. At day 6 cells were counter-stained with antibodies to cell surface markers (e.g. anti-CD4-APC-H7 and biotinylated anti-LLT14F IgG1 followed by APC-conjugated streptavidin) and analysed by flow cytometry. Biotinylated mIgG1 was included as negative control.

Anti-CD3 Induced CD4+ T Cell Activation

CFSE-labelled CD4$^+$ T cells were cultured in RPMI 1640 complete media containing 10% human serum. Anti-CD3 stimulation was performed for 5 days in 48 well plates, precoated overnight at 37° C. with 3 μg/ml anti-CD3 (OKT3; BD). On day 5 cells were counterstained with anti-LLT14F IgG1 followed by the APC-conjugated streptavidin.

Flow-Cytometry

Cells were washed in PBS containing 1% FCS and incubated with relevant fluorochrome-conjugated antibody for 30 min at 4° C. Samples were washed three times in PBS containing 1% FCS and analysed by flow cytometry. Cells stained with biotinylated anti-anti-LLT14F mIgG1 mAb were subsequently washed and incubated with streptavidin-APC for 30 min at 4° C. and washed prior to FACS analysis.

Results

Staining of T cells with CFSE allowed phenotypic analysis of the T cell population after MLR-induced T cell activation using dendritic cells. After stimulation, CFSE-stained T cells were gated on CD4$^+$ cells and analysed for LLT1 expression. A proportion of the T cells proliferated in response to MLR-induced activation as determined by the decrease in CFSE-staining. Analysis of the LLT1 expression pattern using anti-LLT14F mIgG1 mAb and an irrelevant IgG1 as negative isotype control ab shows that the proliferating T cells were positive for LLT1, whereas the resting T cells did not express significant amounts of LLT1 (calculated median fluorescence intensities (MFI) were 1447 and 10, respectively). In line with these data, LLT1 expression was induced on proliferating T cells upon stimulation with plate-bound anti-CD3 antibody. LLT1 was expressed on a high frequency (>70%) of CD3-activated Th1, Th17 and Treg cells as determined by intracellular staining of IFNγ, IL-17 and IL-10, respectively.

Together, these data suggest that T cells up-regulate LLT1 surface expression upon activation.

Examples 9 to 11

Examples 9-11 describe the expression of LLT1 expression in inflamed tissue from patients with tonsillitis, chronic inflammatory bowel diseases (Crohn's disease and ulcerative colitis) and rheumatoid arthritis. Moreover, LLT1 expression in cancer cells from B cell lymphomas is described.

Example 9

LLT1 Expression in Subsets of Tonsilar B and T Lymphocytes

Material and Methods

Tissue Samples

Tonsilar tissue samples were obtained from patients with tonsillitis undergoing tonsillectomy at Rigshospitalet, Copenhagen, Denmark. The study was approved by the local ethical committee.

Samples of inflamed intestine and intestinal tissue samples within normal limits were derived from patients with Crohns Disease and ulcerative colitis and from adenoma patients, respectively, undergoing intestinal resection surgery as part of the medical treatment. All intestinal tissue samples were obtained from Cambridge Bioscience, UK.

Immunohistochemistry

Immunohistochemical staining was performed with anti-LLT12F1A5 on thin sections (4 μm) of formalin-fix and paraffin-embedded cells and tissue samples. After de-paraffination and rehydration, sections were subjected to heat-induced epitope retrieval (HIER) in Tris/EGTA buffer pH9 and to blocking of endogenous biotin and peroxidase activity with Avidin-Biotin system (Dako, Glostrup, Denmark) and 0.5% $H_2O_2$ treatment, respectively. Unspecific protein-binding was blocked with 7% donkey and 3% human serum, 3% bovine serum albumin, 3% skim milk and 0.05% Tween in TBS. Sections were then incubated with 0.1 μg/ml mAb LLT1-2F1 or with an IgG1 isotype control (Mab002, R&D Systems) antibody followed by biotinylated anti-mouse Ig secondary antibody (Jackson Immunolaboratories Inc.). Antibody binding was detected with a series of incubations with avidin-biotin-HRP complex (Vectastain, Vector), biotinylated tyramid (TSA kit, Perkin Elmer) and Vectastain and finally visualized with diaminobenzidine (DAB). Nuclei was counterstained with hematoxylin and mounted in Pertex.

Hematoxylin and Eosin Staining

In parallel, tonsilar tissue sections were stained with hematoxylin and eosin (H&E) according to standard procedure.

Flow Cytometry

Tonsils were obtained from patients undergoing tonsillectomy for tonsillitis. Fresh tonsil tissue was cut into smaller pieces and pressed through a sterile nylon mesh (0.4 μm) to obtain a single cell suspension. To block for unspecific FcR binding the cell suspension was resuspended in PBS/10% foetal calf serum containing human IgG for 20 minutes at 4° C. in the dark. Cells were resuspended in PBS/1% foetal calf serum and incubated with monoclonal antibodies for 30 minutes at 4° C. in the dark.

The following monoclonal antibodies (Becton Dickinson) were used: CD3 Pacific Blue, CD19 APC Cy7, CD62L APC, and CD86 APC. Expression of LLT1 was detected with PE-conjugated anti-LLT14F (4F68-PE). In all experiments gates were set on live and single cells. In all experiments isotype matched controlled were used. Data from gated cells were recorded and the percentage of positive for each analysed marked assessed using the isotype-matched negative control.

Results

Validation of Anti-LLT12F1A5 in the Immunohistochemistry Application

The use of anti-LLT12F1A5 in the IHC application was validated on LLT1-HEK293 cells. Anti-LLT12F1A5 stained HEK293 cells only when these were transfected with LLT1 expression vector. These data demonstrate that anti-LLT12F1A5 recognizes LLT1 in the IHC application.

Expression of LLT on Germinal Center B Cells

Figure 7:
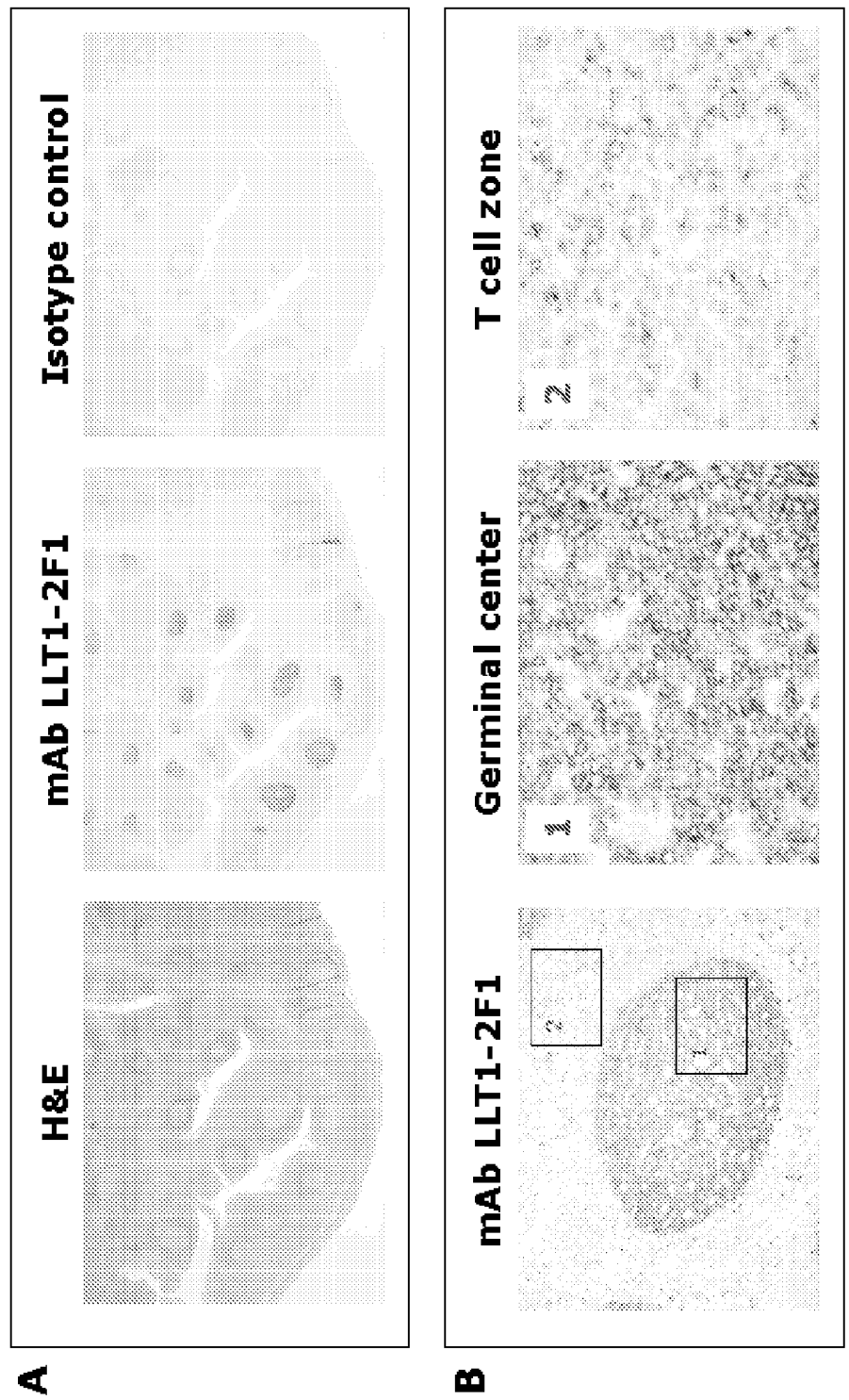
FIG. 7 shows that LLT1 is expressed on subsets of immune cells in tissue samples from tonsillitis patients evaluated by immunohistochemistry.

On tonsilar tissue sections anti-LLT12F1A5 stain B cells that were localized in the germinal centers of B cell follicles (FIG. 7B1). This was confirmed by anti-LLT12F1A5 and anti-CD20 double-immunofluorescence demonstrating co-localization of LLT1 with germinal center B cells but not with B cells localized in other areas of the tonsil. To further evaluate LLT1 expression in tonsil, freshly purified tonsil mononuclear cells were analysed by flow cytometry (FIG. 8). A minor fraction (~10%) of the CD19+ tonsilar B cells stained positive for LLT1 with anti-LLT14F. The LLT1-positive B cells were $CD62L^{low}$ and $CD86^{high}$ (FIG. 8A) indicating that the cells had an activated phenotype. Moreover, LLT1-positive B cells were $CD38^{high}$ and the majority of these were also $CD27^{high}$ (FIG. 8B), indicating that LLT1-positive B cells in the tonsil are germinal center B cells undergoing differentiation to memory B cells.

Expression of LLT1 on a Subset of Tonsilar T Cells

Some of the cells in the parafollicular T cell-rich zone (FIG. 7B2) were weakly positive for anti-LLT12F1A5 staining in the immunohistochemical application. These cells were demonstrated by double immunofluorescence to be double-positive for anti-CD3 staining, suggesting that LLT1 is expressed in a subpopulation of tonsilar T cells. In line with this, LLT1 could be detected on a subset of CD4+ T cells by anti-LLT14F in one of four tonsillitis patients in the flow cytometry application. These LLT1+ CD4+ T cells expressed CD69, indicating an activated phenotype (FIG. 8C).

Conclusion

In conclusion, these data suggest that LLT1 is expressed by activated B cells undergoing somatic hypermutation, expansion and differentiation into memory cells in the germinal centers of B cell follicles. Moreover, LLT1 was observed in a subset of para-follicular CD4+ T cells displaying an activated phenotype. Therefore, LLT1 appears to be present on activated, but not resting B and T lymphocytes.

Example 10

Figure 9:
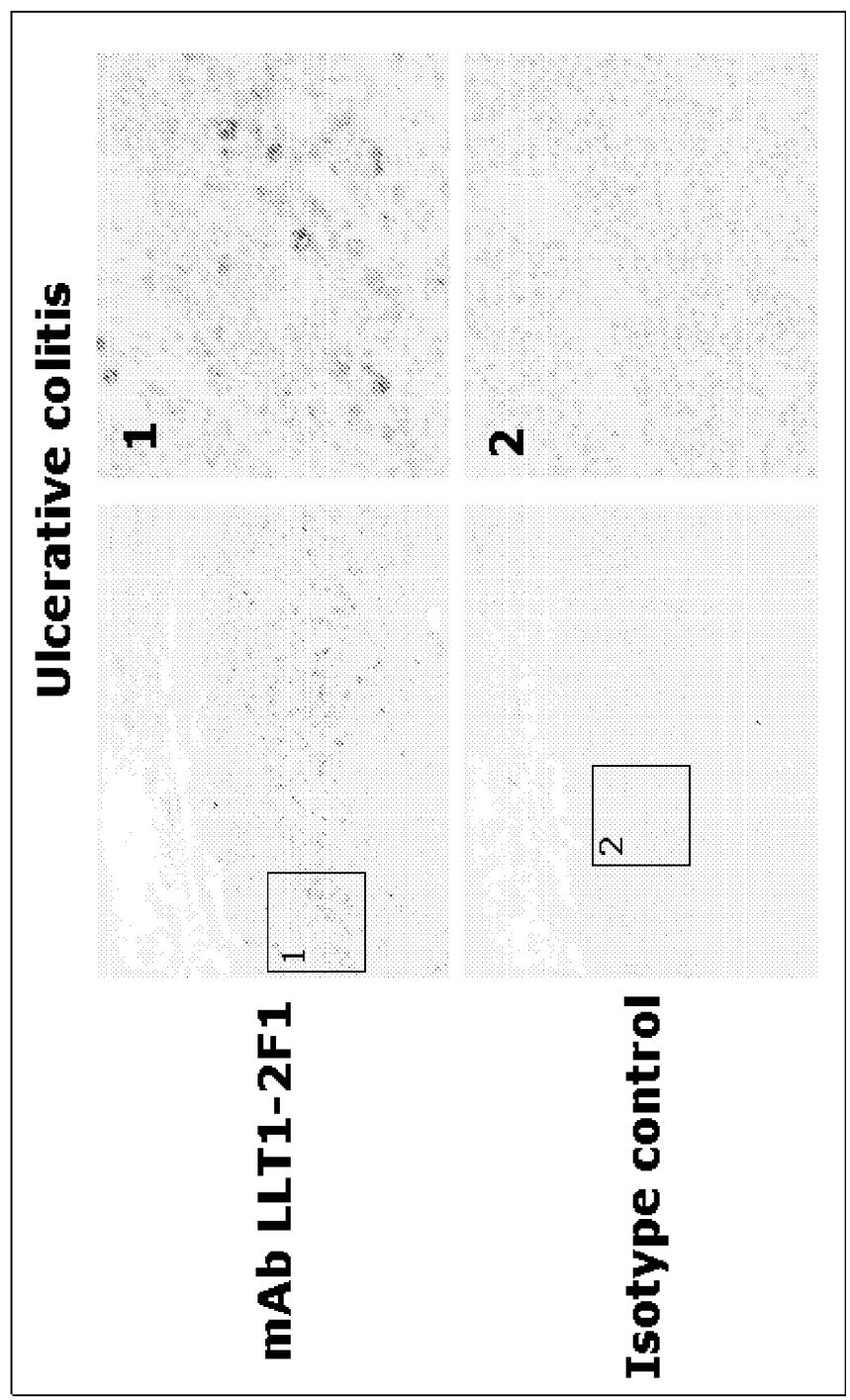
FIG. 9 shows that LLT1 is expressed in the inflamed intestinal tissue of individuals with inflammatory bowel disease (IBD) and in the inflamed synovial tissue of a rheumatoid arthritis (RA) patient.
Figure 9:
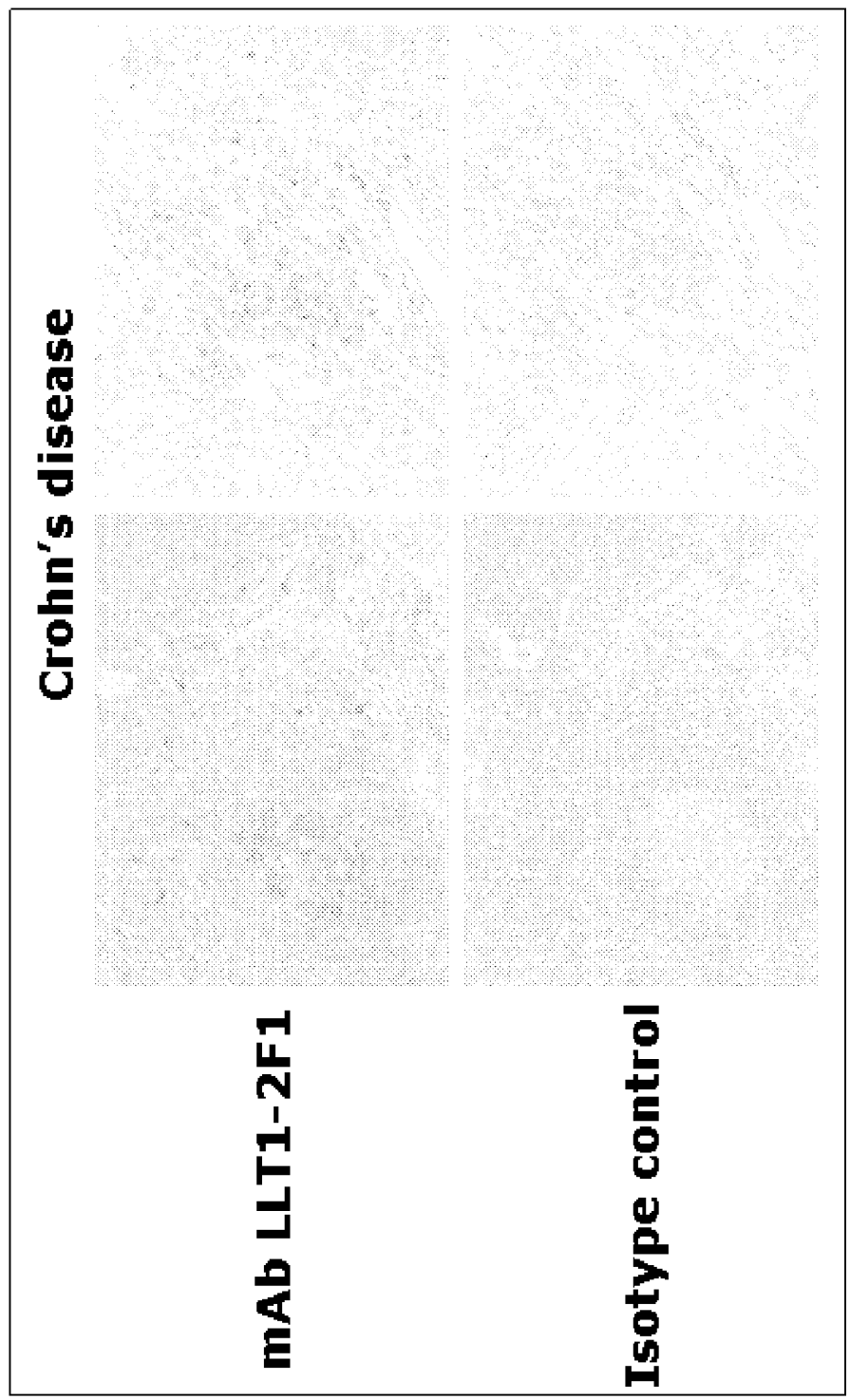
Figure 9:
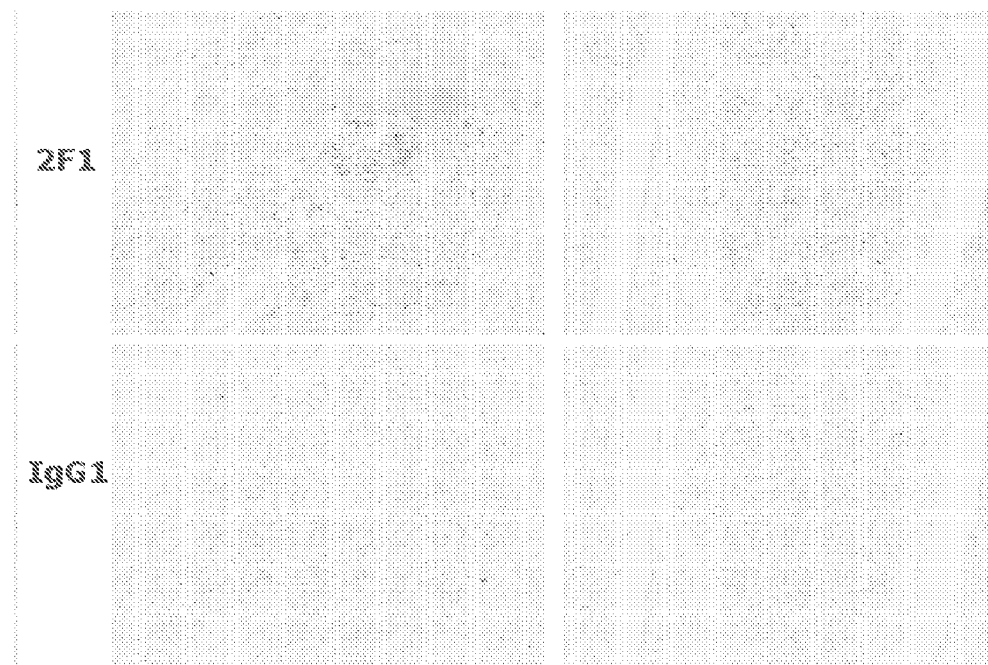

Immunohistochemical Detection of LLT1 Expression in Inflammatory Bowel Disease and Rheumatoid Arthritis The anti-LLT12F1A5 antibody was applied to tissue sections of inflamed intestine from inflammatory bowel disease (IBD) and rheumatoid arthritis patients using the immunohistochemical protocol described in detail in example 7. LLT1+ cells were present among infiltrating immune cells located in pro-inflammatory aggregates in IBD samples from ulcerative colitis and Crohn's disease patients (FIGS. 9A and 9B, respectively). LLT1+ cells were also present among infiltrating immune cells in inflamed synovium tissue samples from rheumatoid arthritis patients (FIG. 9C, lower panel).

In conclusion, blocking the interaction between LLT1 and its receptor CD161 or depleting LLT1+ immune cells with a monoclonal anti-LLT1 antibody such as anti-LLT14F may have beneficial therapeutic effects in IBD and rheumatoid arthritis patients.

Example 11

LLT1 Expression by Human B Cell Lines and Primary B Cell Lymphomas

A number of human cell lines were screened for LLT1 expression by flow cytometry (Table 6). All solid tumour cell lines as well as cell lines derived from osteoblasts, fibroblasts and myoblasts did not express LLT1; neither did HEK293 embryonic nor HUVEC endothelial cells. Among hematopoietic tumour cell lines, LLT1 was expressed by B cell-derived cells lines (Raji, Ramos, BL2, Daudi, SUDHL4, VAL and RL) but not by cell lines derived from acute monocytic and T cell leukemias or from plasma cell leukemia. In addition, LLT1 expression was detected on 2 EBV-transformed B cell lines. These data demonstrate preferential expression of LLT1 on human B cell lines.

TABLE 6

LLT1 surface expression on human cell lines

| Cell lines | LLT1 surface expresson |
|---|---|
| Solid tumor cell lines | |
| HT29, Caco2, C4A, HCA-7 (colon) | – |
| H146 (lung) | – |
| HeLa (cervix) | – |
| Sy54p31 (neuroblastoma) | – |
| M77 (melanoma) | – |
| U373 (glioma) | – |
| Hematopoietic tumor cell lines | |
| THP1 (acute monocytic leukemia) | – |
| Jurkat, Tall (acute T cell leukemia) | – |
| Raji, Ramos, BL2, Daudi (Burkitt's lymphoma) | + |
| SUDHL4, VAL, RL (follicular lymphoma transformed B cell line) | + |
| SKMM2 (plasma cell leukemia) | – |
| EBV-transformed B cell lines | |
| C1R | – |
| 721.221 | + |
| 721.45 | + |
| JY | – |
| Colonna | – |
| Lependu | – |
| Osteoblasts | |
| MG63, SAOS2, CAL72 | – |
| Fibroblasts | |
| HFF-h Tert | – |
| Myoblasts | |
| CP7, C1 diff, SEV P7, SEV diff, 0520 | – |
| (HEK)293 | – |
| HUVEC | – |

LLT1 expression by a selection of non-Hodgkin's lymphomas displayed on a tissue microarray (TMA) slide was analyzed by immunohistochemistry. LLT1+ cancer cells were observed in 24 of the 33 B lymphomas represented on the TMA slide. In 16 of the 24 LLT1+ B lymphomas staining intensity were higher that of normal lymph nodes (Table 7). These data demonstrate frequent expression of LLT1 in B lymphomas.

TABLE 7

LLT1 staining of non-Hodgkin's lymphoma tissue microarray.

| | LLT1 staining: Semi-quantitative score | | | | Frequency of LLT1 positive lymphomas |
|---|---|---|---|---|---|
| | 0 | 1+ | 2+ | 3+ | |
| B small cleaved cell lymphoma | 1 | 1 | 3 | 0 | 4/5 |
| B large cleaved cell lymphoma | 1 | 4 | 2 | 4 | 8/9 |
| B large non-cleaved cell lymphoma | 1 | 2 | 1 | 1 | 4/5 |
| Large B cell lymphoma | 3 | 3 | 2 | 3 | 8/11 |
| Mucosa-ass. B cell lymphoma | 2 | 1 | 0 | 0 | 1/3 |
| Lymphocytic plasmacytoid lymphoma | 0 | 0 | 1 | 0 | 1/1 |
| T cell lymphoma | 0 | 1 | 0 | 0 | 1/1 |
| T lymphocytic lymphoma | 0 | 0 | 0 | 2 | 2/2 |
| Large cell lymphoma | 0 | 0 | 0 | 1 | 1/1 |
| Lymph node | 0 | 1 | 1 | 1 | 3/3 |
| Placenta | 1 | 0 | 0 | 0 | 0/1 |

In conclusion, LLT1+ was expressed on B cell-derived human cell lines and primary B cell lymphomas. Therefore, monoclonal anti-LLT1 antibodies that are able to induce ADCC and CDC may have beneficial therapeutic effect in patients having LLT1-expressing B lymphomas.

Example 12

NK Mediated Cell Killing of LLT1+ Human B Cell Lines is Enhanced by Blocking Anti-LLT1 Antibody To analyse if a blocking anti-LLT1 antibody can enhance NK cell-mediated killing of LLT1-expressing tumor cell lines, NK cells were co-cultured with LLT1+ Raji, SUDHL4 or Ramos cells in the absence or presence of anti-LLT14F antibody (Table 8). NK cell cytotoxicity was measured as % CD107a$^+$ NK cells. Anti-LLT14F antibody increased NK cell-mediated cytotoxicity towards the three cell lines, whereas control antibody had no effect. The anti-CD161 antibody HP3G10 and the anti-HLA ABC antibody DX17 also increased NK cell-mediated cytotoxicity. Observed effects of DX17 and anti-LLT14F were additive. These data suggest that a blocking anti-LLT1 antibody enhances NK cell-mediated killing of LLT1+ cancer cells and thus may be beneficial in the treatment of patients with such cancers.

TABLE 8

Effect of anti-LLT1 antibodies on NK cell degranulation in response to Raji, SUDHL4 and Ramos cells

| % CD107a$^+$ NK cells | Raji | SUDHL4 | Ramos |
|---|---|---|---|
| No mAb | 10.3 | 11.6 | 8.1 |
| mIgG1 | 11.5 | 12 | 7.9 |
| anti-CD161 (HP3G10) | 13.1 | 17.5 | 10.9 |
| anti-LLT14F | 17.2 | 18.8 | 9.7 |
| anti-MHC class I (DX17) | 17.9 | 20.3 | 18 |
| anti-LLT14F + anti-MHC class I (DX17) | 29.9 | 26 | 21.1 |

Example 13

NK Cell-Mediated, Antibody-Dependent Cellular Cytotoxicity (ADCC) of LLT1-Expressing C1R Cells is Triggered by Anti-LLT1 Antibody Material and Methods NK cells were purified from PBMCs and incubated for 4 hours with chromium-labelled C1R or C1R-LLT1 preincubated for 30 minutes with antibodies, either mIgG1, anti-LLT14F or anti-CD20(rituximab, RTX). Specific lysis of C1R or C1R-LLT1 was assessed by measuring chromium release in a multi detector gamma counter (United Technologies Packard). The percentage of specific lysis was calculated as [(experimental re-leased)−(spontaneous release)]/[(maximum release)−(spontaneous release)]×100.

Results

Figure 10:
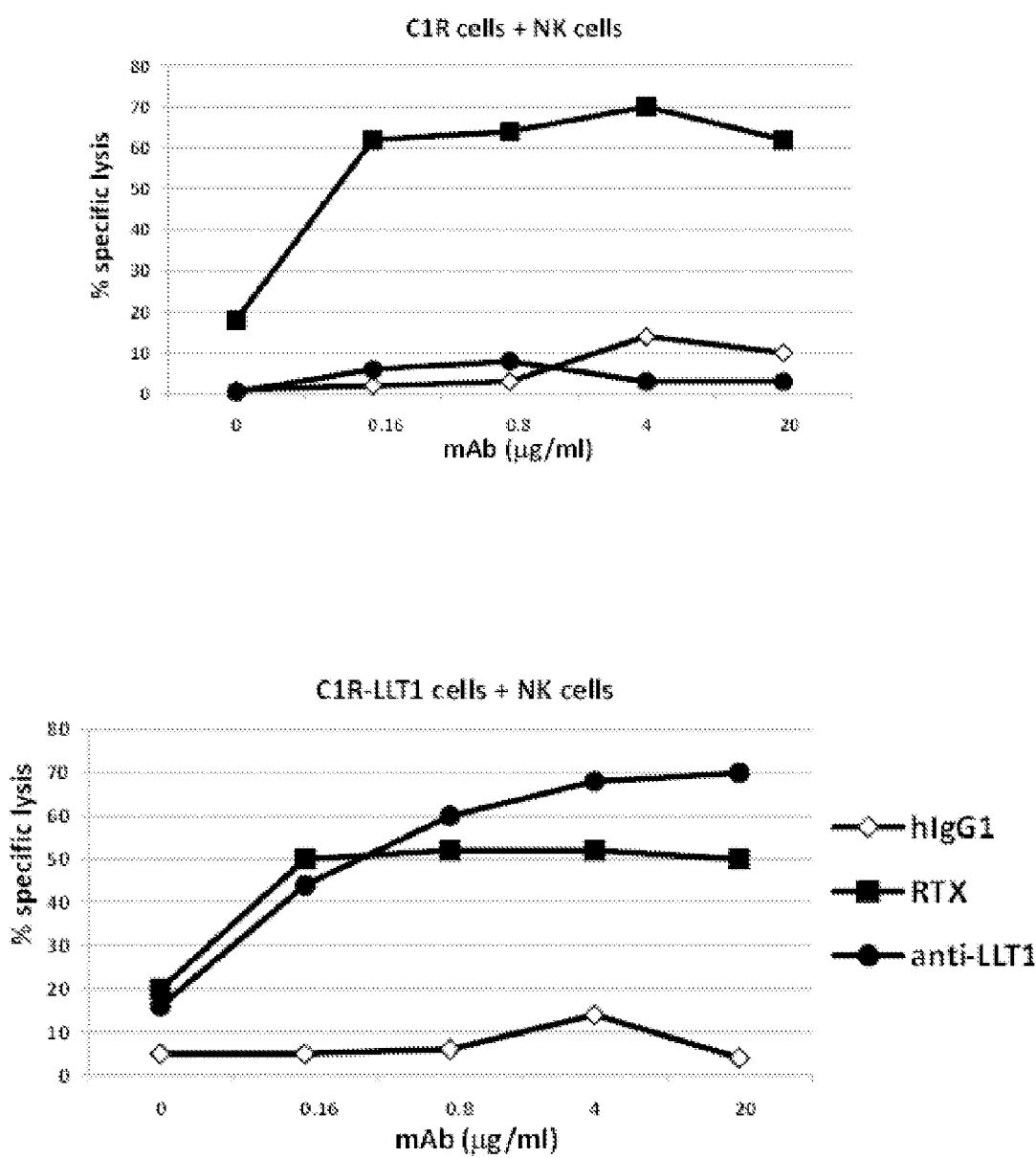
FIG. 10 shows that mAb anti-LLT14F triggers antibody-dependent cellular cytotoxicity (ADCC) of LLT1-expressing C1R cells when incubated with NK cells, similarly to anti-CD20(Rituximab).

C1R and C1R-LLT1 cells express CD20 at their cell surface and are lysed by NK cells through ADCC using the anti-CD20Rituximab at concentrations of 0.16 mg/ml or above (FIG. 10). C1R-LLT1 cells but not C1R cells are lysed by NK cells through ADCC in the presence of anti-LLT14F at concentrations of 0.16 mg/ml or above. Anti-LLT14F shows similar ADCC activity as Rituximab.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention claimed is:

1. A monoclonal antibody which specifically binds to lectin-like transcript 1 (LLT1), wherein the LLT1 comprises SEQ ID NO:1, wherein:
   the heavy chain of said antibody comprises:
   a CDR1 sequence of amino acids 31 to 35 (SYGMS) of SEQ ID NO:4;
   a CDR2 sequence of amino acids 50 to 66 (TINSNG-GRTFYPDSVKG) of SEQ ID NO:4;
   a CDR3 sequence of amino acids 99 to 108 (DGGY-WAHFDY) of SEQ ID NO:4; and
   the light chain of said antibody comprises:
   a CDR1 sequence of amino acids 24 to 40 (RSSQSIVH-SNGNTYLE) of SEQ ID NO:7;
   a CDR2 sequence of amino acids 56 to 62 (KVSNRFS) of SEQ ID NO:7; and
   a CDR3 sequence of amino acids 94 to 102 (FQGSH-VPWT) of SEQ ID NO:7.

2. A monoclonal antibody which specifically binds to lectin-like transcript 1 (LLT1), wherein the LLT1 comprises SEQ ID NO:1, wherein the light chain of said antibody comprises SEQ ID NO: 7 and the heavy chain of said antibody comprises SEQ ID NO : 4.

3. A pharmaceutical formulation that comprises the monoclonal antibody according to claim 1.

4. A pharmaceutical formulation that comprises the monoclonal antibody according to claim 2.

* * * * *